(12) United States Patent
Yun et al.

(10) Patent No.: US 11,160,504 B2
(45) Date of Patent: Nov. 2, 2021

(54) ELECTRONIC DEVICE FOR MEASURING BIOMETRIC INFORMATION

(71) Applicant: Samsung Electronics Co., Ltd., Gyeonggi-do (KR)

(72) Inventors: In Ho Yun, Gyeonggi-do (KR); Jong Ho Park, Seoul (KR); Jee Hoon Lee, Seoul (KR); Doo Suk Kang, Gyeonggi-do (KR); Jeong Min Park, Gyeonggi-do (KR)

(73) Assignee: Samsung Electronics Co., Ltd

( * ) Notice: Subject to any disclaimer, the term of this patent is extended or adjusted under 35 U.S.C. 154(b) by 443 days.

(21) Appl. No.: 15/901,322

(22) Filed: Feb. 21, 2018

(65) Prior Publication Data

US 2018/0235542 A1 Aug. 23, 2018

(30) Foreign Application Priority Data

Feb. 21, 2017 (KR) .......................... 10-2017-0022827

(51) Int. Cl.
*A61B 5/00* (2006.01)
*G16H 40/63* (2018.01)
*A61B 5/0205* (2006.01)
*A61B 5/0531* (2021.01)
*G06F 3/041* (2006.01)
*A61B 5/1455* (2006.01)
*A61B 5/024* (2006.01)
(Continued)

(52) U.S. Cl.
CPC .......... *A61B 5/6843* (2013.01); *A61B 5/0205* (2013.01); *A61B 5/681* (2013.01); *G16H 40/63* (2018.01); *A61B 5/002* (2013.01); *A61B 5/02427* (2013.01); *A61B 5/0531* (2013.01); *A61B 5/0533* (2013.01); *A61B 5/14552* (2013.01); *A61B 5/25* (2021.01); *A61B 5/291* (2021.01); *A61B 5/296* (2021.01); *A61B 5/398* (2021.01); *G06F 3/041* (2013.01); *G06F 2203/04101* (2013.01)

(58) Field of Classification Search
CPC .............. A61B 5/68; A61B 5/00; A61B 5/681
See application file for complete search history.

(56) References Cited

U.S. PATENT DOCUMENTS 9,861,280 B2   1/2018  Lee
2005/0075553 A1* 4/2005  Sakai .................... A61B 5/721
                                                         600/372
(Continued)

FOREIGN PATENT DOCUMENTS

KR   1020050103355   10/2005
KR      101564073    10/2015

*Primary Examiner* — Lynsey C Eiseman
(74) *Attorney, Agent, or Firm* — The Farrell Law Firm, P.C.

(57) ABSTRACT

Disclosed is an electronic device including a plurality of electrodes selectively connectable to a touch sensor or one or more biometric sensors; and a processor configured to receive a user input through the plurality of electrodes in a state in which the touch sensor and the plurality of electrodes are connected; perform an operation relating to the touch sensor when where the user input satisfies a first condition; connect the plurality of electrodes to the one or more biometric sensors when where the user input satisfies a second condition; and obtain a plurality of pieces of biometric information according to a pre-determined sequence through the plurality of electrodes connected with the one or more biometric sensors.

10 Claims, 14 Drawing Sheets

(51) Int. Cl.
    *A61B 5/0533*     (2021.01)
    *A61B 5/25*       (2021.01)
    *A61B 5/291*      (2021.01)
    *A61B 5/296*      (2021.01)
    *A61B 5/398*      (2021.01)

(56)            References Cited

U.S. PATENT DOCUMENTS

| | | | |
|---|---|---|---|
| 2014/0257129 A1* | 9/2014 | Choi | A61B 5/296 |
| | | | 600/546 |
| 2015/0245782 A1* | 9/2015 | Morland | A61B 5/065 |
| | | | 600/301 |
| 2016/0026212 A1* | 1/2016 | Lee | G06F 1/3231 |
| | | | 361/679.03 |
| 2016/0029911 A1* | 2/2016 | Lee | A61B 5/681 |
| | | | 600/301 |
| 2016/0058311 A1* | 3/2016 | Kondo | A61B 5/681 |
| | | | 600/479 |
| 2016/0066845 A1* | 3/2016 | Kwon | A61B 5/6826 |
| | | | 600/384 |
| 2016/0106337 A1* | 4/2016 | Jung | A61B 5/681 |
| | | | 600/547 |
| 2016/0192856 A1* | 7/2016 | Lee | A61B 5/0006 |
| | | | 600/384 |
| 2017/0020449 A1* | 1/2017 | Shim | A61B 5/002 |
| 2017/0027461 A1  | 2/2017 | Shin | |
| 2018/0220923 A1* | 8/2018 | Shim | A61B 5/0537 |

* cited by examiner

ELECTRONIC DEVICE FOR MEASURING BIOMETRIC INFORMATION

PRIORITY

This application is based on and claims priority under 35 U.S.C. § 119 to Korean Patent Application No. 10-2017-0022827, filed on Feb. 21, 2017, in the Korean Intellectual Property Office, the disclosure of which is incorporated by reference herein in its entirety.

BACKGROUND

1. Field

The present disclosure relates generally to a technology for measuring biometric information.

2. Description of Related Art

With the development of mobile communication technologies, electronic devices, such as smartphones, tablet computers, etc., have become widely used. The electronic devices may be worn on the user's body to measure the user's biometric information. For example, the electronic devices may measure the user's blood oxygen saturation, photoplethysmograph (PPG), heart rate (HR), galvanic skin response (GSR), electrocardiography (ECG), bioelectrical impedance (BIA), etc.

The electronic devices may include a plurality of components to measure the aforementioned biometric information. For example, the electronic devices may measure blood oxygen saturation, PPG, an HR, etc. through optical sensors. Furthermore, the electronic devices may measure GSR, ECG, etc. through electrode sensors (e.g., a GSR sensor, an ECG sensor, etc.).

Since the electronic devices cannot simultaneously or continuously control the plurality of components, the electronic devices cannot simultaneously or continuously measure the aforementioned biometric information. For example, if a user wants to measure PPG, GSR, and ECG, the user has to change a measurement state every time by touching a display (or a button). Therefore, the users may find it inconvenient to measure the biometric information and thus may not use the electronic devices.

SUMMARY

Aspects of the present disclosure are to address at least the above-mentioned problems and/or disadvantages and to provide at least the advantages described below. Accordingly, an aspect of the present disclosure is to provide an electronic device for solving the above-mentioned problems and disadvantages.

In accordance with an aspect of the present disclosure, an electronic device includes a plurality of electrodes selectively connectable to a touch sensor or one or more biometric sensors; and a processor configured to receive a user input through the plurality of electrodes in a state in which the touch sensor and the plurality of electrodes are connected; perform an operation relating to the touch sensor when the user input satisfies a first condition; connect the plurality of electrodes to the one or more biometric sensors when the user input satisfies a second condition; and obtain a plurality of pieces of biometric information according to a pre-determined sequence through the plurality of electrodes connected with the one or more biometric sensors.

In accordance with an aspect of the present disclosure, an electronic device includes a housing including a first electrode and a second electrode; a first sensor selectively connectable to the first electrode or the second electrode; a second sensor selectively connectable to the first electrode or the second electrode; and a processor configured to receive a user input for measuring biometric information through the first electrode or the second electrode; connect the first electrode or the second electrode with the first sensor, based at least on the user input; obtain first biometric information relating to the first sensor through an electrode connected with the first sensor; connect the first electrode or the second electrode with the second sensor after obtaining the first biometric information; and obtain second biometric information relating to the second sensor through the first electrode or the second electrode connected with the second sensor.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1A:
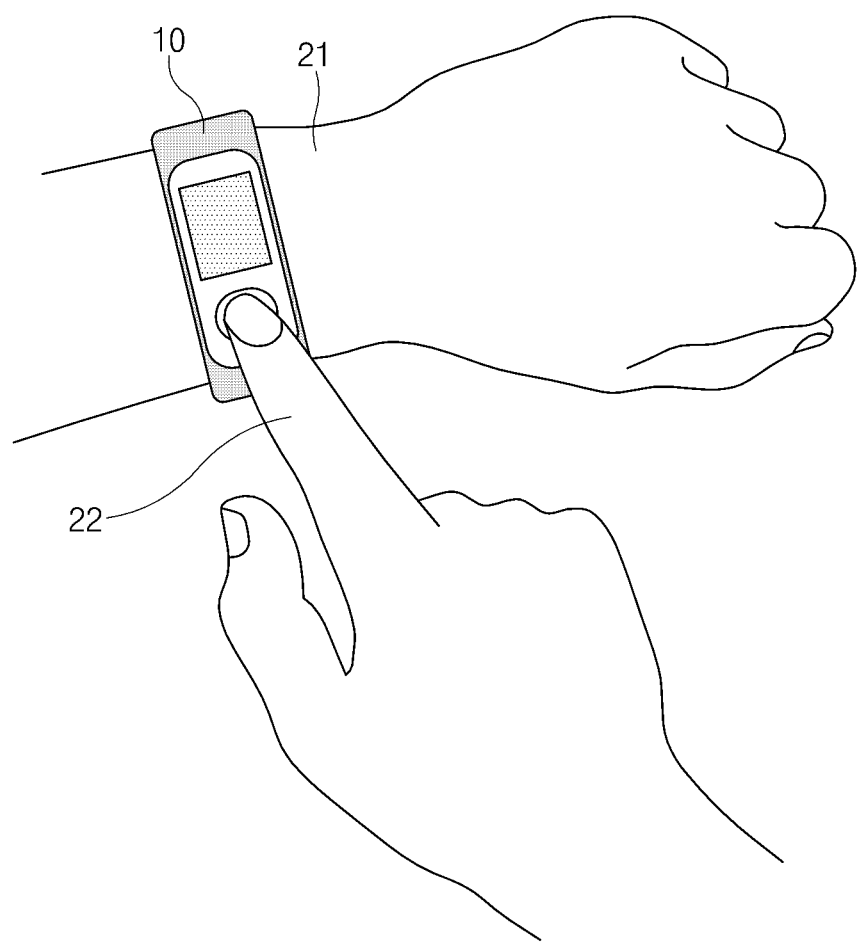
FIG. 1A illustrates an operating environment of an electronic device, according to an embodiment of the present disclosure.

Those of ordinary skill in the art will recognize that modifications, equivalents, and/or alternatives on the various embodiments described herein can be made without departing from the scope and spirit of the present disclosure. In the present disclosure, the expressions "have", "may have", "include", "comprise", "may include", and "may comprise" used herein indicate existence of corresponding features (e.g., elements such as numeric values, functions, operations, or components) but do not exclude the presence of additional features.

The expression "configured to" used in the present disclosure may be used interchangeably with the expressions "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor (AP)) which performs corresponding operations by executing one or more software programs which are stored in a memory device.

Terms used in the present disclosure are used to describe particular embodiments and are not intended to limit the scope of the present disclosure. The terms of a singular form may include plural forms unless there is a contextually distinctive difference. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal sense unless expressly so defined in various embodiments of the present disclosure. In some cases, even if terms are terms which are defined in the present disclosure, they are not to be interpreted to exclude embodiments of the present disclosure.

An electronic device according to various embodiments of the present disclosure may include smartphones, tablet personal computers (PCs), mobile phones, video telephones, electronic book readers, desktop PCs, laptop PCs, netbook computers, workstations, servers, personal digital assistants (PDAs), portable multimedia players (PMPs), motion picture experts group (MPEG-1 or MPEG-2) audio layer 3 (MP3) players, mobile medical devices, cameras, or wearable devices. The wearable device may include an accessory type (e.g., watches, rings, bracelets, anklets, necklaces, glasses, contact lens, or head-mounted devices (HMDs), a fabric or garment-integrated type (e.g., an electronic apparel), a body-attached type (e.g., a skin pad or tattoos), or a bio-implantable type (e.g., an implantable circuit).

According to various embodiments of the present disclosure, the electronic device may be a home appliance. The home appliances may include televisions (TVs), digital versatile disc (DVD) players, audio players and recorders, refrigerators, air conditioners, cleaners, ovens, microwave ovens, washing machines, air cleaners, set-top boxes, home automation control panels, security control panels, TV boxes (e.g., Samsung HomeSync™, Apple TV™, and Google TV™, game consoles (e.g., Xbox™ and PlayStation™, electronic dictionaries, electronic keys, camcorders, electronic picture frames, etc.

According to an embodiment of the present disclosure, an electronic device may include various medical devices (e.g., portable medical measurement devices (e.g., a blood glucose monitoring device, a heartbeat measuring device, a blood pressure measuring device, a body temperature measuring device, etc.), a magnetic resonance angiography (MRA) device, a magnetic resonance imaging (MRI) device, a computed tomography (CT) device, a scanner, and an ultrasonic device), navigation devices, global navigation satellite system (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller machines (ATMs), points of sales (POSs) devices, or Internet of things (IoT) devices (e.g., light bulbs, various sensors, electric or gas meters, sprinkler devices, fire alarms, thermostats, street lamps, toasters, exercise equipment, hot water tanks, heaters, boilers, etc.).

According to an embodiment of the present disclosure, the electronic device may include parts of furniture or buildings/structures, electronic boards, electronic signature receiving devices, projectors, or various measuring instruments (e.g., water meters, electricity meters, gas meters, or wave meters, etc.). The electronic device may be one of the above-described devices or a combination thereof. An electronic device may be a flexible electronic device. Furthermore, an electronic device is not limited to the above-described electronic devices and may include other electronic devices and new electronic devices according to the development of technologies.

In the present disclosure, the term "user" may refer to a person who uses an electronic device or may refer to a device (e.g., an artificial intelligence (AI) electronic device) that uses the electronic device.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. The electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B", "at least one of A and B", "at least one of A or B", "A, B, or C", "at least one of A, B, and C", and "at least one of A, B, or C" may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to", "connected with", or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic", "logic block", "part", or "circuitry". A module may be a single integral component, or a minimum unit or part thereof, adapted to perform one or more functions. For example, according to an embodiment of present disclosure, the module may be implemented in a form of an application specific integrated circuit (ASIC).

Various embodiments as set forth herein may be implemented as software (e.g., the program 940) including one or more instructions that are stored in a storage medium (e.g., internal memory or external memory) that is readable by a machine (e.g., the electronic device 901). For example, a processor (e.g., the processor 920) of the machine (e.g., the electronic device 901) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. While, the term "non-transitory" simply means that the storage medium is a tangible device, and does not include a signal (e.g., an electromagnetic wave), this term does not differentiate between where data is semi-permanently stored in the storage medium and where the data is temporarily stored in the storage medium.

According to an embodiment of present disclosure, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of present disclosure, each component (e.g., a module or a program) of the above-described components may include a single entity or multiple entities. One or more of the above-described components may be omitted, or one or more other components may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. Operations performed by the module, the program, or another component may be carried out sequentially, in parallel, repeatedly, or heuristically, or one or more of the operations may be executed in a different order or omitted, or one or more other operations may be added.

Figure 1B:
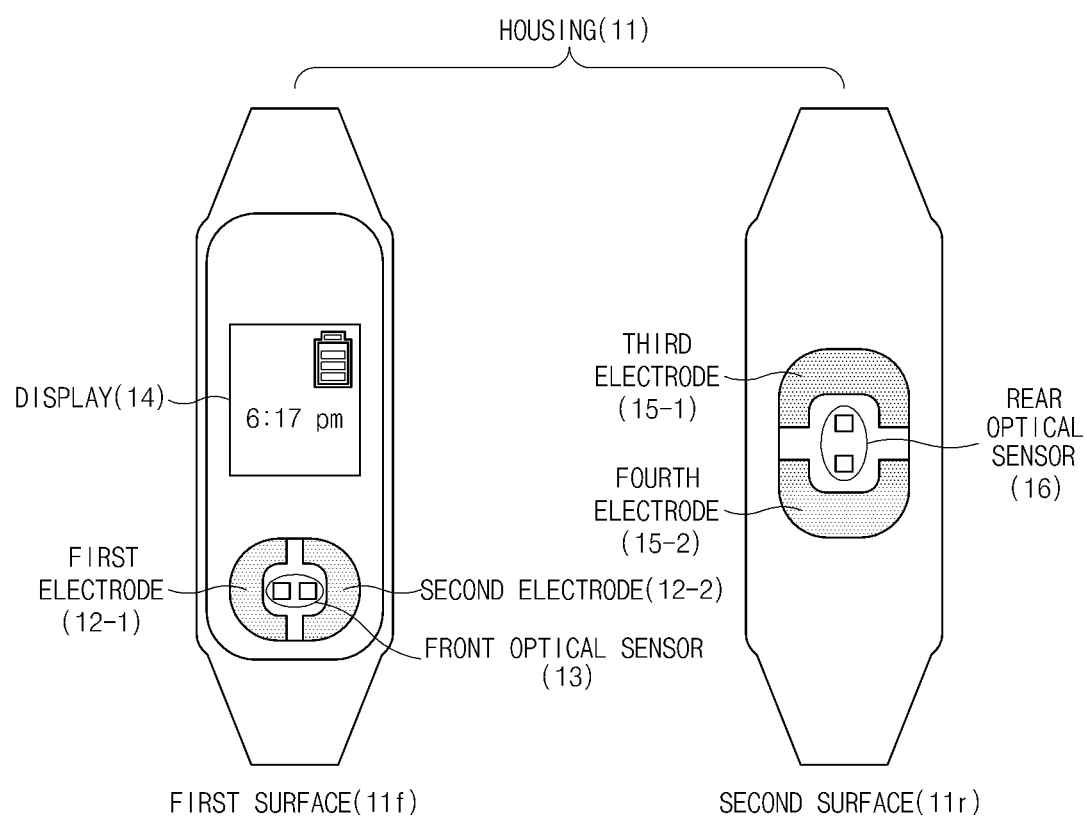
FIG. 1B illustrates a front side and a rear side of an electronic device, according to an embodiment of the present disclosure.

FIG. 1A illustrates an operating environment of an electronic device, according to an embodiment of the present disclosure. FIG. 1B illustrates a front side and a rear side of an electronic device, according to an embodiment of the present disclosure.

Referring to FIG. 1A, an electronic device 10 (e.g., a wearable device) may be worn on a user's body. For example, the electronic device 10 may be worn on the user's wrist 21, like a watch or may be worn on the user's arm, like an arm band. Furthermore, the electronic device 10 may be mounted on the user's head, like an HMD or may be worn over the user's face, like eyeglasses.

The user, wearing the electronic device 10, may place a part of the user's body on the electronic device 10. As illustrated in FIG. 1A, the user may touch a finger 22 to a sensor area of the electronic device 10 in the state in which the electronic device 10 is worn on the user's wrist 21.

Referring to FIG. 1B, the electronic device 10 may include a housing 11, a first electrode 12-1, a second electrode 12-2, a front optical sensor 13, a display 14, a third electrode 15-1, a fourth electrode 15-2, and a rear optical sensor 16.

The housing 11 may include a first surface 11*f*, a second surface 11*r*, and side surfaces. In the present disclosure, the first surface 11*f* may be referred to as a front surface of the electronic device 10, and the second surface 11*r* may be referred to as a rear surface of the electronic device 10. The side surfaces may surround a space between the first surface 11*f* and the second surface 11*r*.

The components disposed on the rear surface 11*r* of the housing 11 will be described first. The third electrode 15-1, the fourth electrode 15-2, and the rear optical sensor 16 may be exposed through the rear surface 11*r*.

The electronic device 10 may determine whether the electronic device 10 is worn on the user's body, through the third electrode 15-1 or the fourth electrode 15-2. For example, if the rear surface 11*r* is brought into contact with the user's wrist 21, the third electrode 15-1 or the fourth electrode 15-2 may also be brought into contact with the wrist 21. If the third electrode 15-1 or the fourth electrode 15-2 is brought into contact with the wrist 21, a touch sensor may determine that the electronic device 10 is worn on the user's body.

The electronic device 10 may obtain biometric information through the rear optical sensor 16. If the rear surface 11*r* is brought into contact with the user's wrist 21, the rear optical sensor 16 may emit light toward the wrist 21. The light emitted by the rear optical sensor 16 may be reflected by the wrist 21 and then input to the rear optical sensor 16. The rear optical sensor 16 may obtain biometric information on the basis of the input light. The rear optical sensor 16 may obtain a blood oxygen saturation, a PPG, and an HR.

The first electrode 12-1, the second electrode 12-2, the front optical sensor 13, and the display 14 may be exposed through the front surface 11*f*.

The electronic device 10 may obtain biometric information through the first electrode 12-1 or the second electrode 12-2. For example, the user's finger 22 may make contact with the first electrode 12-1 or the second electrode 12-2 in the state in which the rear surface 11*r* is brought into contact with the wrist 21. If the finger 22 makes contact with the first electrode 12-1 or the second electrode 12-2, a closed loop may be formed, and a biometric sensor may obtain biometric information on the basis of current flowing in the closed loop. For example, the biometric sensor may obtain a GSR, an ECG, a BIA, an electromyography (EMG), an electroencephalography (EEG), an electrooculography (EOG), etc. The "closed loop" used herein may refer to an electrical path formed when the electronic device 10 and the user's body make contact with each other.

The electronic device 10 may obtain biometric information through the front optical sensor 13. For example, if the user's finger 22 is brought into contact with the first electrode 12-1 or the second electrode 12-2, the front optical sensor 13 may obtain a blood oxygen saturation, a PPG, etc. Unless otherwise noted, the description of the rear optical sensor 16 may also be applied to the front optical sensor 13.

The display 14 may output biometric information obtained by the biometric sensor. For example, the display 14 may output a PPG, a GSR, an ECG, and a BIA in the sequence in which they are obtained.

According to an embodiment of the present disclosure, in the case where the electronic device 10 is in a condition where the electronic device 10 cannot obtain biometric information, the electronic device 10 may output the condition through the display 14. For example, if an error occurs in the optical sensor 13 and/or optical sensor 16, or the electrode 12-1, electrode 12-2, electrode 15-1, and/or electrode 15-2, the electronic device 10 may output the error in the optical sensor 13 and/or optical sensor 16, or the electrode 12-1, electrode 12-2, electrode 15-1, and/or electrode 15-2 through the display 14. The electronic device 10 may transmit the condition to an external device (e.g., a smartphone, TV, etc.). If the condition is transmitted to the external device, the external device may output the condition.

Figure 2:
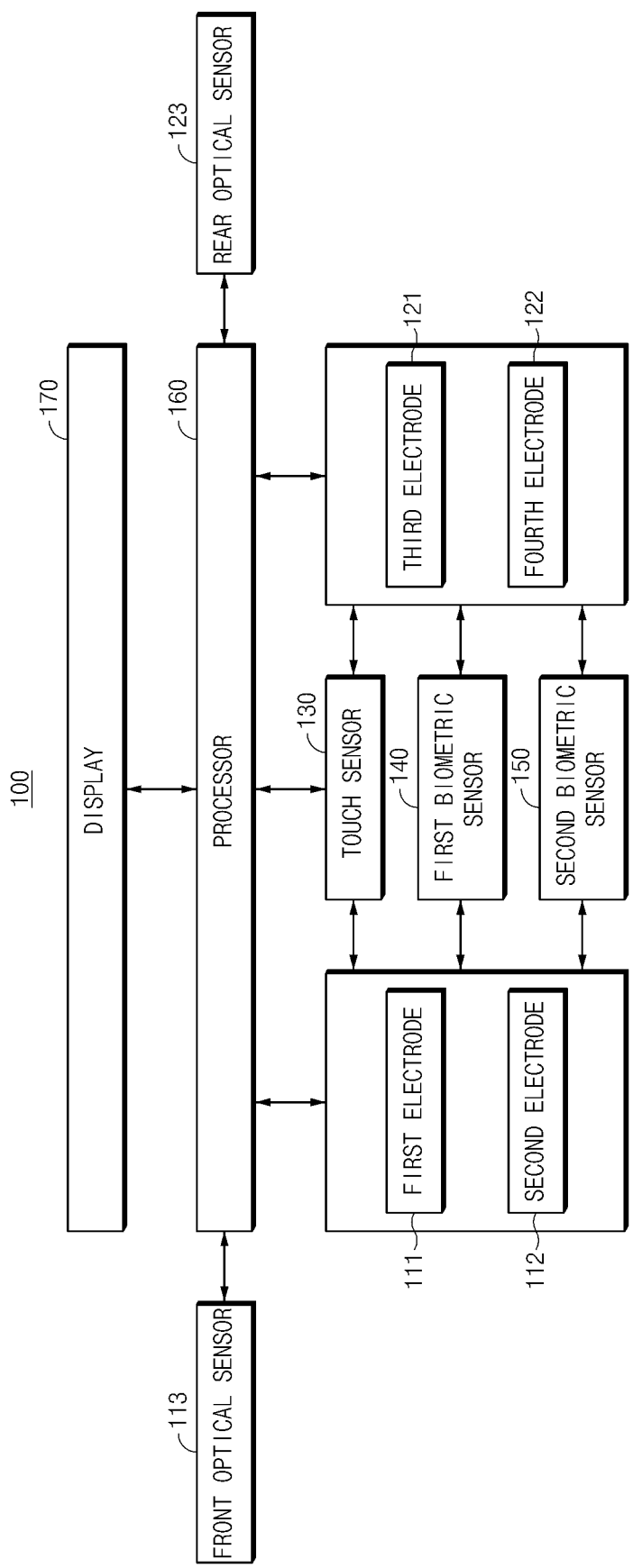
FIG. 2 is a block diagram of an electronic device, according to an embodiment of the present disclosure.

FIG. 2 is a block diagram of an electronic device according, to an embodiment of the present disclosure.

Referring to FIG. 2, an electronic device 100 may include a first electrode 111, a second electrode 112, a front optical sensor 113, a third electrode 121, a fourth electrode 122, a rear optical sensor 123, the touch sensor 130, the first biometric sensor 140, a second biometric sensor 150, a processor 160, and a display 170. The touch sensor 130 may determine whether the electronic device 100 is worn on a user's body. The touch sensor 130 may be electrically connected with the third electrode 121 and the fourth electrode 122. If the third electrode 121 or the fourth electrode 122 is brought into contact with the user's wrist, the touch sensor 130 may determine that the electronic device 100 is worn on the user's body.

Furthermore, the touch sensor 130 may determine whether a part (e.g., a finger) of the user's body is brought into contact with a front surface of the electronic device 100. The touch sensor 130 may be electrically connected with the first electrode 111 and the second electrode 112. If a finger is brought into contact with the first electrode 111 or the second electrode 112, the touch sensor 130 may determine that a part of the user's body is brought into contact with the first electrode 111 or the second electrode 112.

The first biometric sensor 140 and the second biometric sensor 150 may obtain the user's biometric information. For example, if the user's finger is brought into contact with the first electrode 111 or the second electrode 112 while the electronic device 100 is worn on the user's body, the first biometric sensor 140 may obtain a GSR, and the second biometric sensor 150 may obtain an ECG. The first biometric sensor 140 and the second biometric sensor 150 may correspond to any one of a sensor for obtaining a GSR, a sensor for obtaining an ECG, and a sensor for obtaining a BIA. The processor 160 may connect the first biometric sensor 140 or the second biometric sensor 150 with the first electrode 111, the second electrode 112, the third electrode 121, or the fourth electrode 122. For example, if the user's finger is brought into contact with the first electrode 111 and the second electrode 112 while the electronic device 100 is worn on the user's body, the processor 160 may connect the first electrode 111 (or the third electrode 121) and the second electrode 112 (or the fourth electrode 122) with the first biometric sensor 140. In the case where the first biometric sensor 140 is a GSR sensor, the processor 160 may obtain a GSR on the basis of a closed loop formed by the first electrode 111, the second electrode 112, and the first biometric sensor 140, and current flowing in the closed loop.

Furthermore, if the user's finger is brought into contact with the first electrode 111 and the second electrode 112 while the electronic device 100 is worn on the user's body, the processor 160 may connect the second electrode 112 (or the first electrode 111) and the fourth electrode 122 (or the third electrode 121) with the second biometric sensor 150. In the case where the second biometric sensor 150 is an ECG sensor, the processor 160 may obtain an ECG on the basis of a closed loop formed by the second electrode 112, the fourth electrode 122, and the second biometric sensor 150, and current flowing in the closed loop.

Figure 3:
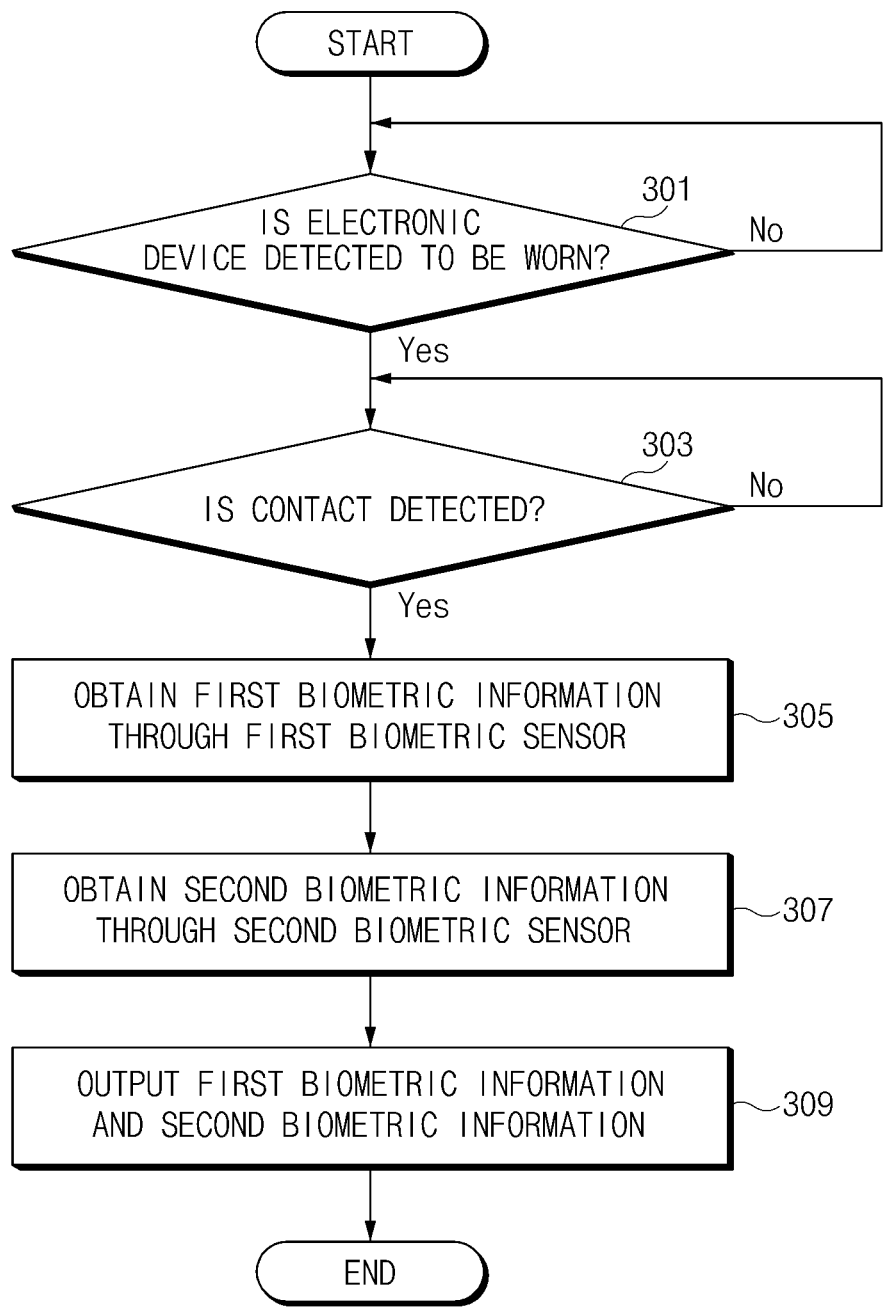
FIG. 3 is a flowchart illustrating an operation of an electronic device, according to an embodiment of the present disclosure.

FIG. 3 is a flowchart illustrating an operation of an electronic device, according to an embodiment of the present disclosure.

Referring to FIG. 3, in step 301, the electronic device 100 may detect whether the electronic device 100 is worn on a user's body. For example, if the user's wrist is brought into contact with the third electrode 121 or the fourth electrode 122, the electronic device 100 may determine that the electronic device 100 is worn on the user's body.

If the electronic device 100 is determined to be worn in step 301, in step 303, the electronic device 100 may detect contact with the user's body. For example, if a finger is brought into contact with the first electrode 111 or the second electrode 112, the electronic device 100 may determine that the user's body is brought into contact with the electronic device 100. If the electronic device 100 is determined not to be worn in step 301, step 301 may be repeated.

If contact is determined in step 303, then in step 305, the electronic device 100 may obtain the first biometric information through the first biometric sensor 140. For example, the electronic device 100 may obtain a GSR in the state in which the electronic device 100 is determined to be worn and the contact is maintained. If the first biometric information is obtained, the electronic device 100 may, in step 307, obtain second biometric information through the second biometric sensor 150. For example, the electronic device 100 may obtain an ECG.

If the first biometric information and the second biometric information are obtained, the electronic device 100 may, in step 309, output the first biometric information and the second biometric information on the display 170. The electronic device 100 may sequentially or simultaneously output the first biometric information and the second biometric information.

If contact is determined not to happen in step 303, then step 303 is repeated.

Figure 4A:
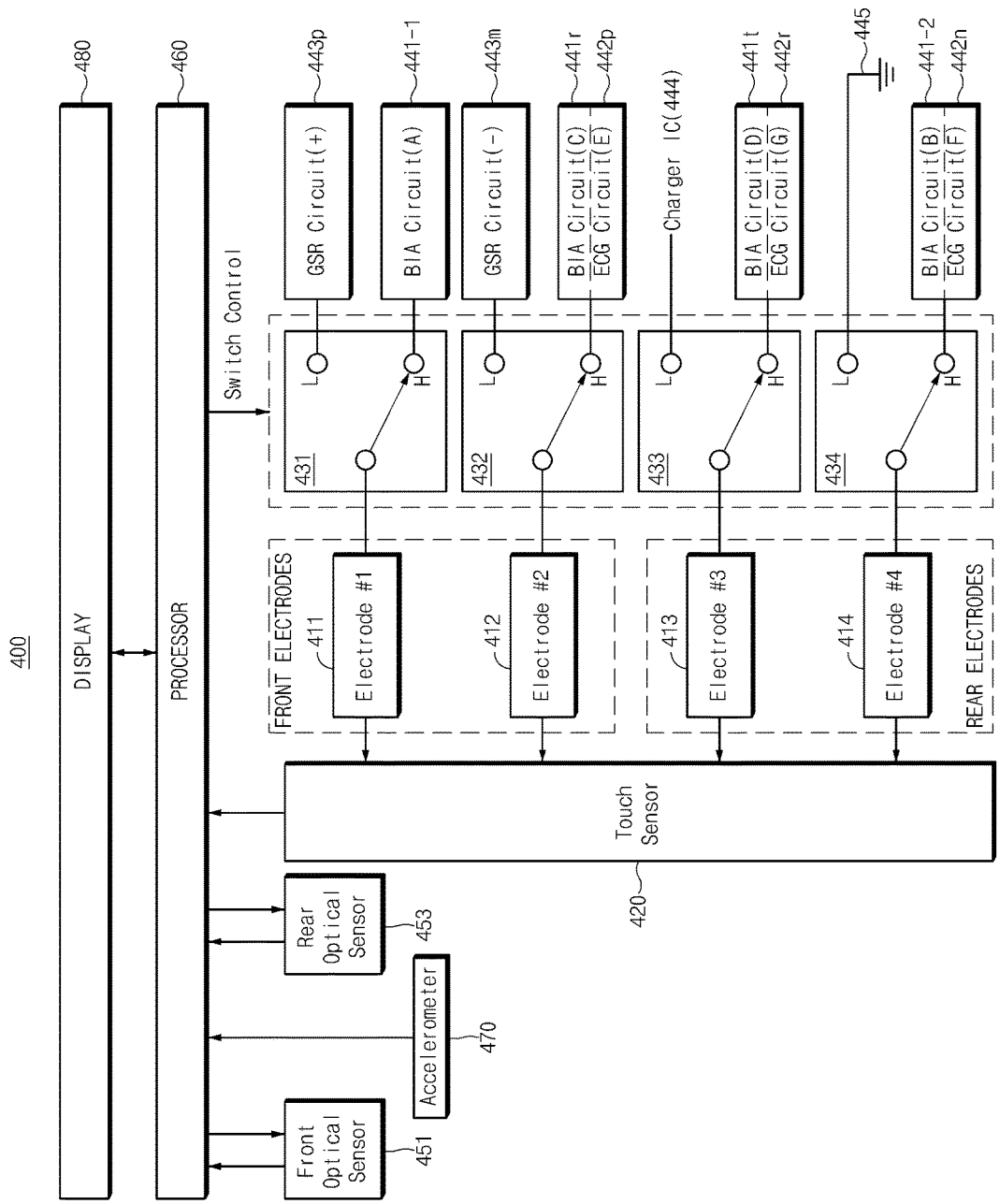
FIG. 4A is a block diagram of an electronic device, according to an embodiment of the present disclosure.
Figure 4B:
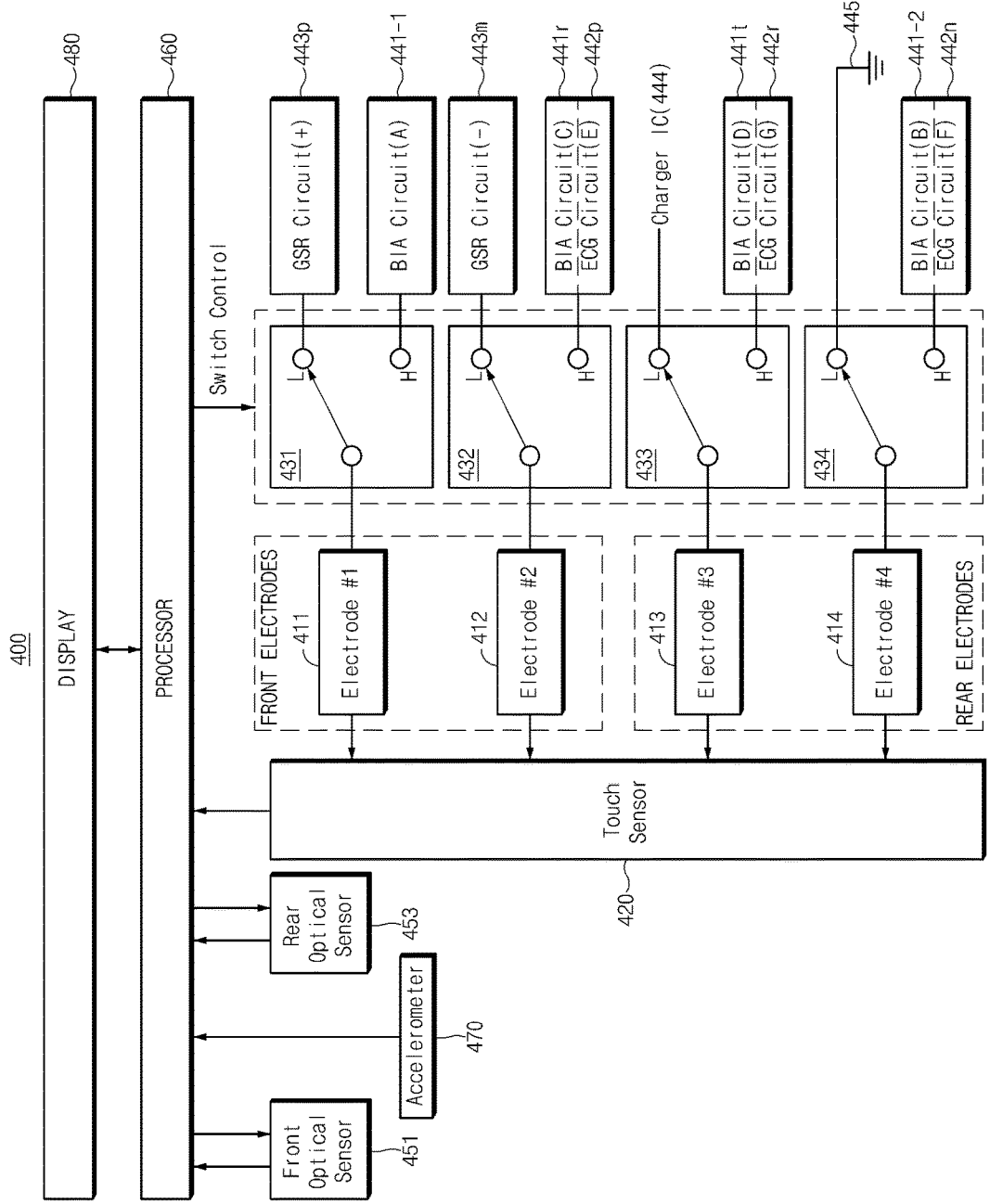
FIG. 4B is a block diagram of an electronic device, according to an embodiment of the present disclosure.

FIG. 4A is a block diagram of an electronic device, according to an embodiment of the present disclosure. FIG. 4B is a block diagram of an electronic device, according to an embodiment of the present disclosure. Unless otherwise noted, the descriptions of the front optical sensor 13 and the rear optical sensor 16 may also be applied to a front optical sensor 451 and a rear optical sensor 453. Furthermore, the description of the touch sensor 130 may also be applied to a touch sensor 420. Descriptions of FIGS. 4A and 4B will be given under the assumption that an electronic device is worn on a user's body and a part (e.g., a finger) of the user's body is brought into contact with a front surface of the electronic device.

Referring to FIG. 4A, an electronic device 400 may obtain a BIA and an ECG. A process of obtaining the BIA will be described. An A terminal 441-1 of a BIA sensor and a first electrode 411 may be connected through a first switch 431, and a B terminal 441-2 of the BIA sensor and a fourth electrode 414 may be connected through a fourth switch 434. Furthermore, a C terminal 441r of the BIA sensor and a second electrode 412 may be connected through a second switch 432, and a D terminal 441t of the BIA sensor and a third electrode 413 may be connected through a third switch 433. The A terminal 441-1 of the BIA sensor may generate current, and the current may flow through the B terminal 441-2 of the BIA sensor. At this time, a processor 460 may measure a voltage value applied between the C terminal 441r of the BIA sensor and the D terminal 441t of the BIA sensor to obtain a BIA.

A process of obtaining the ECG will be described. An E terminal 442p of an ECG sensor and the second electrode 412 may be connected through the second switch 432, and a F terminal 442n of the ECG sensor and the fourth electrode 414 may be connected through the fourth switch 434. At this time, a G terminal 442r of the ECG sensor and the third electrode 413 may be connected through the third switch 433. The E terminal 442p of the ECG sensor may generate current, and the current may flow through the F terminal 442n of the ECG sensor. The processor 460 may obtain an ECG on the basis of the current flowing through the F terminal 442n of the ECG sensor.

Referring to FIG. 4B, the electronic device 400 may obtain a GSR. The GSR may be obtained by using electrodes located on the front surface of the electronic device 400. For example, a positive electrode 443p of a GSR sensor and the first electrode 411 may be connected through the first switch 431, and a negative electrode 443m of the GSR sensor and the second electrode 412 may be connected through the second switch 432. The processor 460 may obtain a GSR on the basis of current flowing from the positive electrode 443p to the negative electrode 443m of the GSR sensor.

According to an embodiment of the present disclosure, the electronic device 400 may be charged in the case where the electronic device 400 is not worn. For example, a charger IC 444 and the third electrode 413 may be connected through the third switch 433, and the fourth electrode 414 and a ground part 445 may be connected through the fourth switch 434. At this time, a battery connected with the third electrode 413 and the fourth electrode 414 may be charged by the charger IC. Power charged in the battery may be used to obtain biometric information when the electronic device 400 is worn.

According to an embodiment of the present disclosure, the electronic device 400 may include an accelerometer 470 and a motor. The accelerometer 470 may detect a movement of the electronic device 400. For example, the electronic device 400 may stop obtaining biometric information if a very large movement of the electronic device 400 is detected by the accelerometer 470.

The motor may vibrate if the electronic device 400 is worn and in contact with a human body. If the motor vibrates, a user may recognize that the electronic device 400 is ready to measure biometric information.

According to an embodiment of the present disclosure, the electronic device 400 may detect the wearing and the contact through the touch sensor 420 and the front optical sensor 451 and the rear optical sensor 453. For example, the touch sensor 420 may determine whether the electronic device 400 is worn or not, through the third electrode 413 and the fourth electrode 414. In this case, the rear optical sensor 453 may determine the wrist is in contact with the electronic device 400 on the basis of light reflected by the wrist. If light emitted by the rear optical sensor 453 is reflected by the wrist and returns within a very short period of time, the electronic device 400 may determine that the electronic device 400 is worn. By detecting the wearing and the contact by using the touch sensor 420, the front optical sensor 451, and the rear optical sensor 453, the wearing and the contact may be accurately determined.

According to an embodiment of the present disclosure, in the case where the electronic device 400 is in an environment in which the electronic device 400 cannot obtain biometric information, the electronic device 400 may output, on a display 480, the reason why the electronic device 400 cannot obtain biometric information. For example, if the user moves rapidly, the electronic device 400 may detect and output the movement warning message on the display 480.

According to an embodiment of the present disclosure, the electronic device 400 may obtain biometric information in the case where the electronic device 400 is in the environment. The electronic device 400 may obtain biometric information for an extended amount of time during which electrodes and a biometric sensor are connected. Furthermore, the electronic device 400 may obtain biometric information by amplifying the strength of a signal to be transmitted to the biometric sensor.

Figure 5:
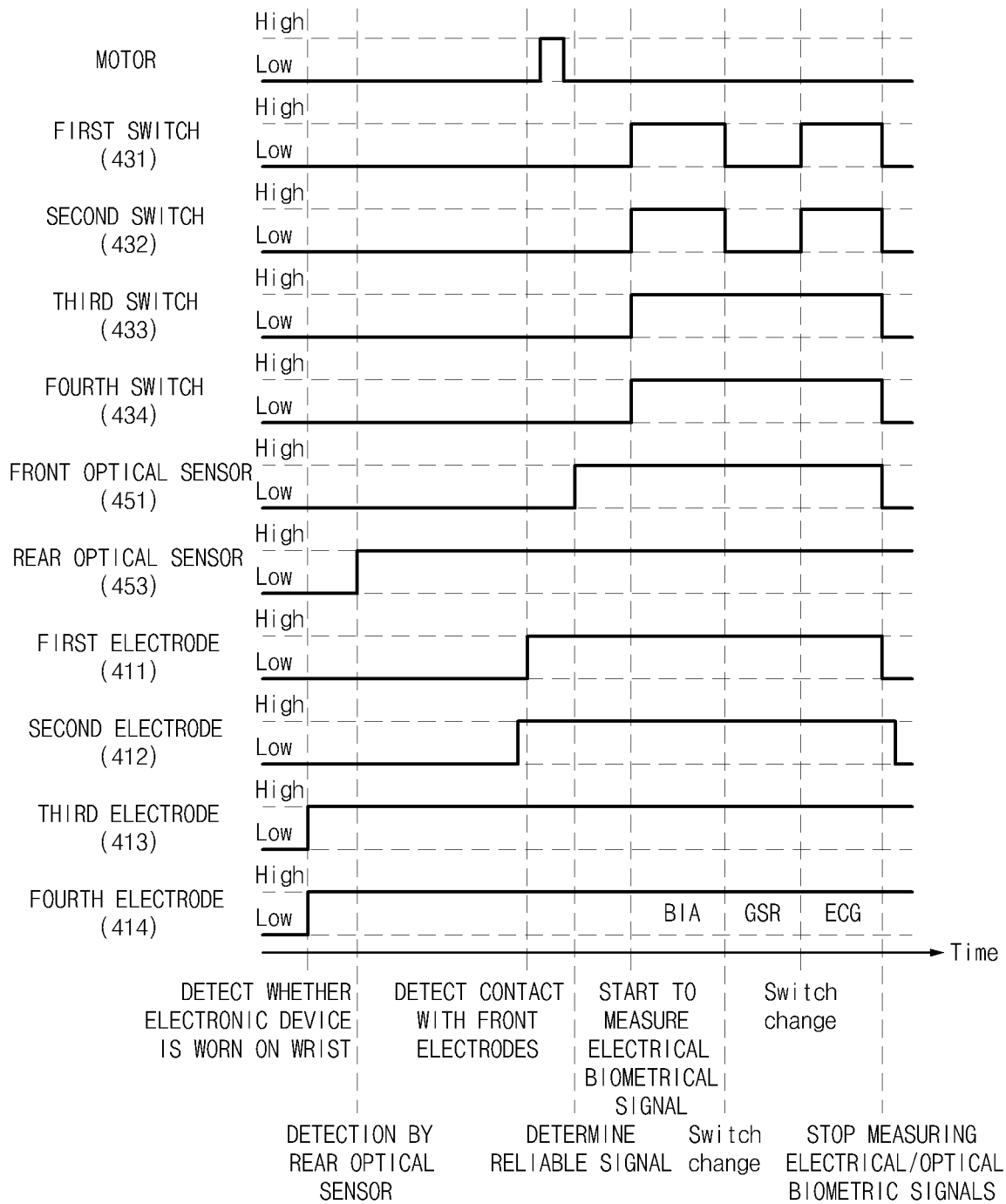
FIG. 5 is a timing diagram of an electronic device, according to an embodiment of the present disclosure.

FIG. 5 is a timing diagram of the electronic device 400, according to an embodiment of the present disclosure. The timing diagram illustrated in FIG. 5 represents the timing of the electronic device 400. In FIG. 5 a high state may refer to a state in which a sensor or an electrode is activated or turned on by switching. In contrast, a low state may refer to a state in which the sensor or the electrode is deactivated or turned off by switching.

Referring to FIG. 5, if the electronic device 400 is worn on a user's wrist, the touch sensor 420 may detect whether the electronic device 400 is worn or not, through the third electrode 413 or the fourth electrode 414. For example, if the electronic device 400 is worn on the wrist, the third electrode 413 or the fourth electrode 414 may change to a high state, and the touch sensor 410 may detect the change.

If the electronic device 400 is detected to be worn on the wrist, the rear optical sensor 453 may change to a high state. The rear optical sensor 453 may obtain the PPG of an object (e.g., a person or an animal) on which the electronic device 400 is worn. If the obtained PPG is within a pre-determined range, the rear optical sensor 453 may determine the object to be a person.

If a part (e.g., a finger) of the user's body is brought into contact with the first electrode 411 or the second electrode 412 while the electronic device 400 is worn, the touch sensor 420 may detect the contact. If a finger is brought into contact with the first electrode 411 or the second electrode 412, the first electrode 411 or the second electrode 412 may change to a high state, and the touch sensor 420 may detect the change. At this time, the motor may vibrate to inform the user of the contact.

The front optical sensor 451 may obtain biometric information in the state in which the wearing is detected and the contact is maintained. For example, the front optical sensor 451 may obtain at least one of blood oxygen saturation (SpO2), an HR, and stress levels. At this time, if the SpO2 is within a pre-determined range, the front optical sensor 451 may determine that the object brought into contact with the first electrode 411 and the second electrode 412 is a person.

The processor 460 may obtain biometric information by controlling the switches in the state in which the wearing is detected and the contact is maintained. For example, the processor 460 may obtain biometric information by selectively connecting the first to fourth switches 431 to 434 with the GSR sensor, the ECG sensor, and the BIA sensor. The contents described with reference to FIGS. 4A and 4B may be applied to a specific operation of obtaining the biometric information. Although FIG. 5 illustrates that the electronic device 400 obtains biometric information in the sequence of a BIA, a GSR, and an ECG, the sequence in which biometric information is obtained is not limited thereto.

Figure 6:
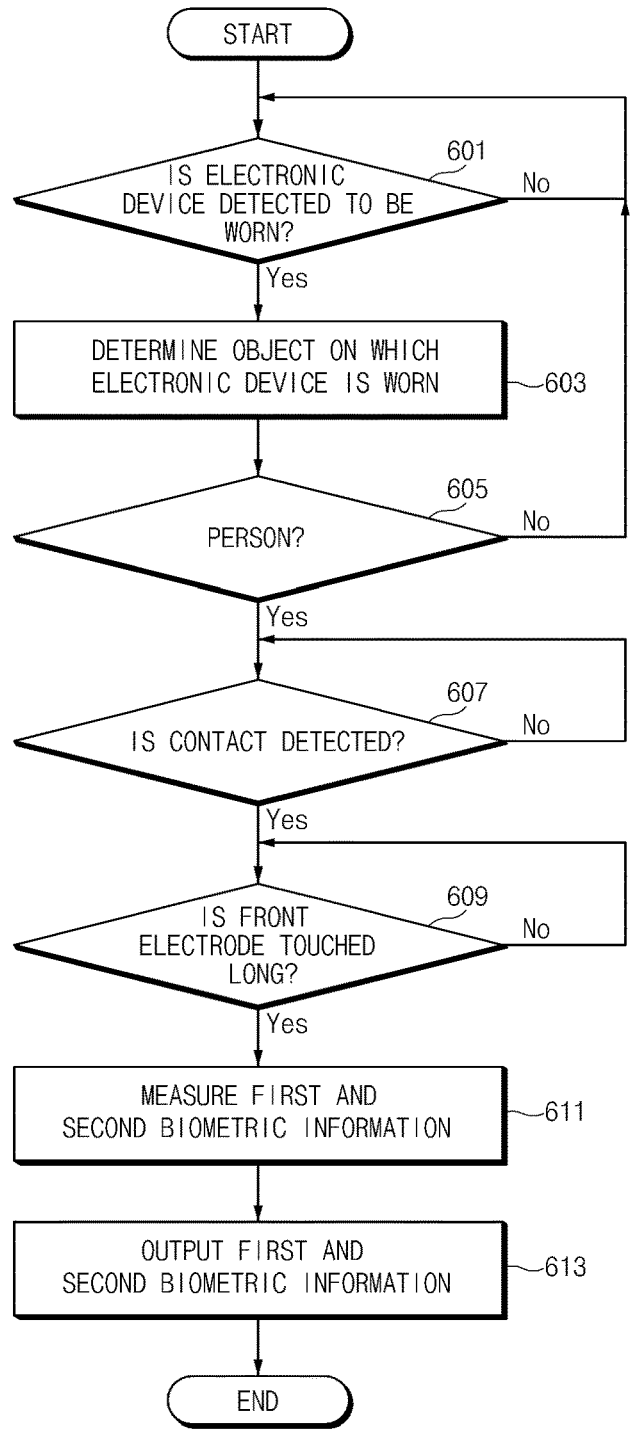
FIG. 6 is a flowchart illustrating an operation of an electronic device, according to an embodiment of the present disclosure.

FIG. 6 is a flowchart illustrating an operation of an electronic device, according to an embodiment of the present disclosure. The flowchart illustrated in FIG. 6 is a flowchart illustrating an operation of the electronic device 400.

Referring to FIG. 6, in step 601, the electronic device 400 may determine whether the electronic device 400 is worn. For example, the electronic device 400 may determine whether the electronic device 400 is worn, depending on whether the third electrode 413 or the fourth electrode 414 is brought into contact with a user's wrist.

If the electronic device 400 is determined to be worn in step 601, in step 603, the electronic device 400 may determine the type of the object on which the electronic device 400 is worn. For example, the electronic device 400 may obtain a PPG through the rear optical sensor 453 in the state in which the wearing is maintained. If the obtained PPG is within a pre-determined range, the electronic device 400 may, in step 605, determine the object to be a person and may perform step 607. If the obtained PPG is outside the pre-determined range, the electronic device 400 may determine that the electronic device 400 is worn on an object (e.g., an animal) that is not a person, and may perform step 601. If the electronic device 400 is determined to not to be worn in step 601, step 601 may be repeated.

In step 607, the electronic device 400 may determine whether a part of the user's body is brought into contact with the front surface of the electronic device 400. For example, if a finger is brought into contact with the first electrode 411 or the second electrode 412, the electronic device 400 may determine that a part of the user's body is brought into contact with the front surface of the electronic device 400. If in step 607 it is determined the user's body is not in contact with electronic device 400, then step 607 may be repeated.

In step 609, the electronic device 400 may determine whether the user makes contact with the electronic device 400 to obtain biometric information. For example, if the time during which a finger is brought into contact with the first electrode 411 or the second electrode 412 is longer than or equal to a predetermined period of time (e.g., a long touch), the electronic device 400 may determine that the user makes contact with the electronic device 400 to obtain biometric information. In contrast, if the time is shorter than the predetermined period of time, the electronic device 400 may determine the contact to be a simple contact (e.g., may determine that the finger grazes the first electrode 411 or the second electrode 412) and step 609 may be repeated.

According to an embodiment of the present disclosure, in step 609, the electronic device 400 may determine whether the user makes contact with the electronic device 400 to obtain biometric information, based on the strength of the contact. If the strength of the contact between the finger and the first electrode 411 or the second electrode 412 is greater than or equal to a pre-determined value, the electronic device 400 may determine that the user makes contact with the electronic device 400 to obtain biometric information.

If the front electrode is touched for a long time in step 609, then in step 611, the electronic device 400 may obtain the first biometric information and the second biometric information. For example, the electronic device 400 may obtain a GSR by using the GSR sensor and an ECG by using the ECG sensor. If the first biometric information and the second biometric information are obtained, the electronic device 400 may, in step 613, output the first biometric information and the second biometric information on the display 480.

Figure 7A:
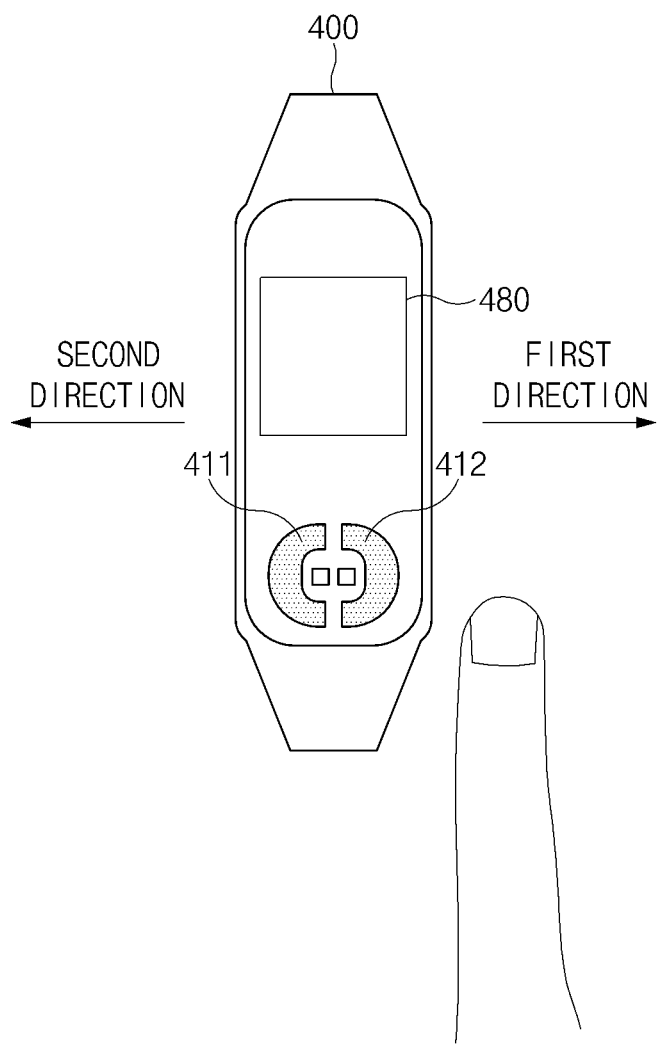
FIG. 7A illustrates an operating environment of an electronic device according, to an embodiment of the present disclosure.
Figure 7B:
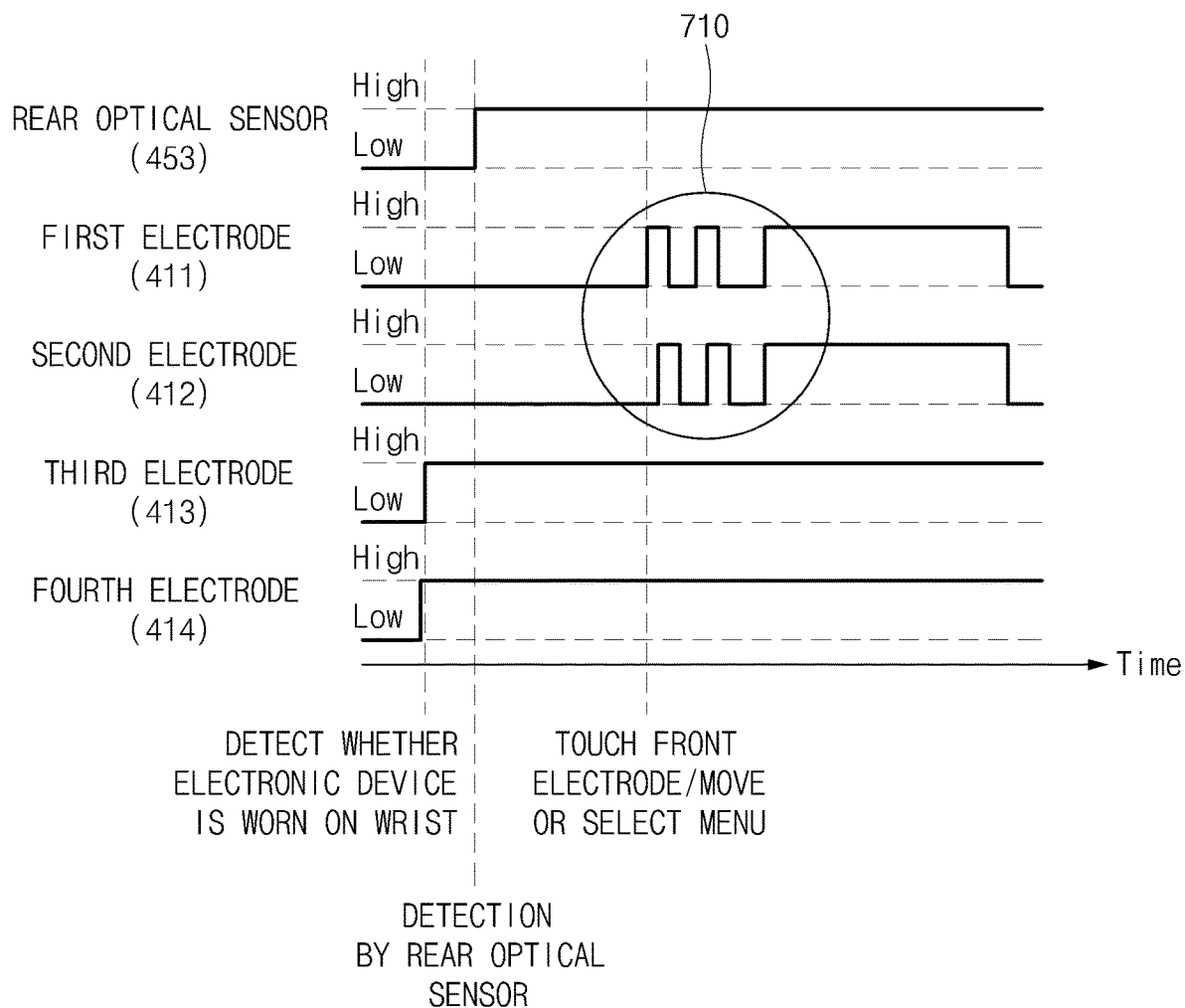
FIG. 7B is a timing diagram of an electronic device, according to an embodiment of the present disclosure.

FIG. 7A illustrates an operating environment of an electronic device, according to an embodiment of the present disclosure. FIG. 7B is a timing diagram of the electronic device 400, according to an embodiment of the present disclosure.

Referring to FIG. 7A, the electronic device 400 may change a state of obtaining biometric information according to a user's touch. For example, if the user sequentially touches the first electrode 411 and the second electrode 412 while moving a finger in a first direction in a state of obtaining the GSR, the electronic device 400 may change to a state of obtaining an ECG. If the state changes, the electronic device 400 may obtain biometric information corresponding to the changed state. Furthermore, the electronic device 400 may output the biometric information corresponding to the changed state on the display 480.

If the user sequentially touches the second electrode 412 and the first electrode 411 while moving the finger in a second direction, the electronic device 400 may return to the state of obtaining a GSR from the state of obtaining the ECG. If the state changes, the electronic device 400 may obtain biometric information corresponding to the changed state and may output the obtained value on the display 480.

Referring to FIG. 7B, it may be identified that the first electrode 411 and the second electrode 412 may change to a high state at different timings in a region 710. That is, if the first electrode 411 changes to a high state prior to the second electrode 412, the electronic device 400 may determine that the user touches the first electrode 411 and the second electrode 412 while moving a finger in the first direction. In contrast, if the second electrode 412 changes to a high state prior to the first electrode 411, the electronic device 400 may determine that the user touches the second electrode 412 and the first electrode 411 while moving a finger in the second direction.

Figure 8:
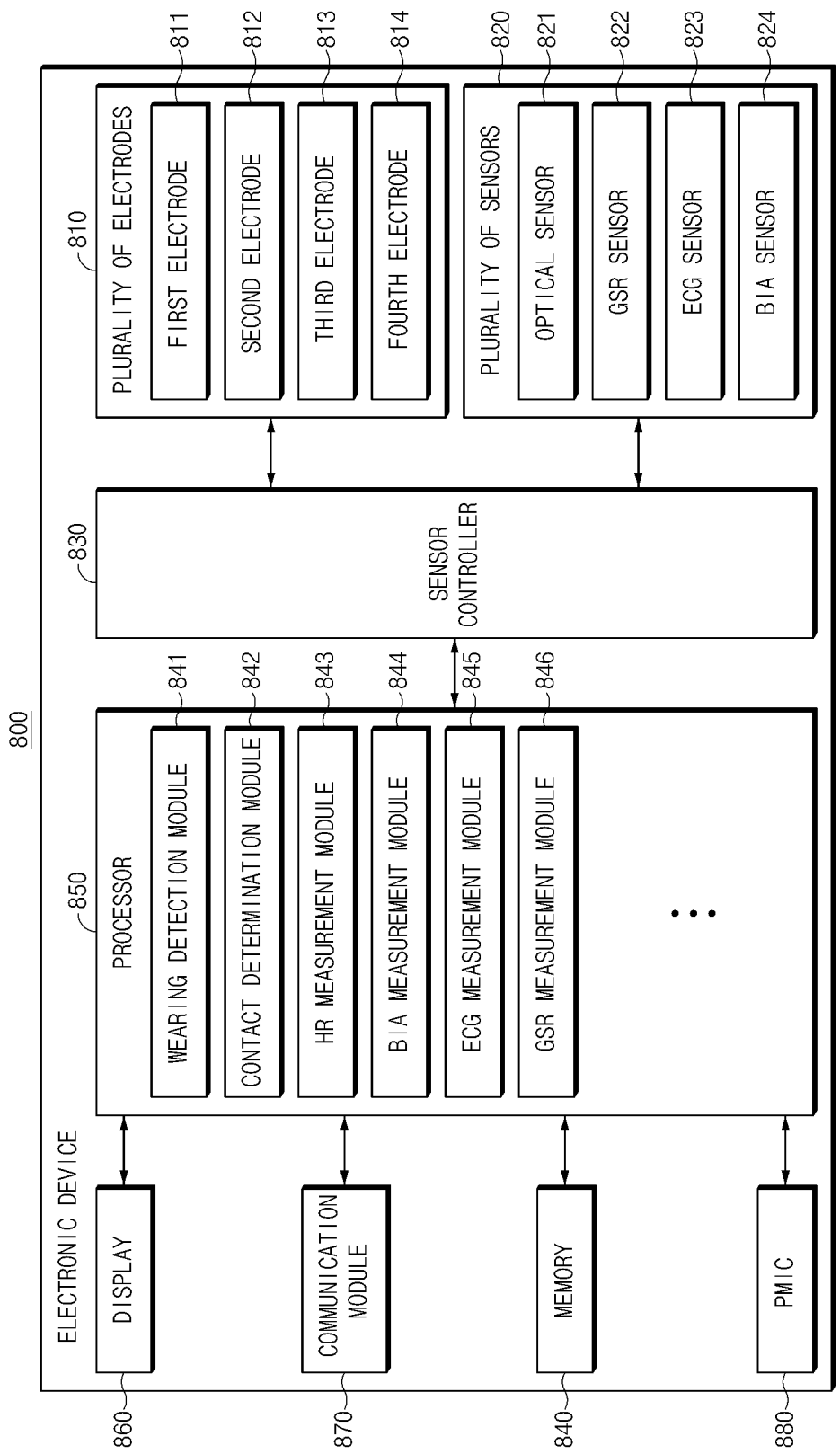
FIG. 8 is a block diagram of an electronic device, according to an embodiment of the present disclosure.

FIG. 8 is a block diagram of an electronic device, according to an embodiment of the present disclosure.

Referring to FIG. 8, an electronic device 800 may include a plurality of electrodes 810, a plurality of sensors 820, a sensor controller 830, a memory 840, a processor 850, a display 860, a communication module 870, and a power management IC (PMIC) 880.

The plurality of electrodes 810 may be terminals having a conductive material included therein or coated thereon, and may pass electric charges. For example, the plurality of electrodes 810 may make direct contact with a user's body (e.g., a finger) to pass electric charges through the user's body.

According to an embodiment of the present disclosure, a cover glass may be disposed on the plurality of electrodes 810. Since the cover glass is disposed on the plurality of electrodes 810, the plurality of electrodes 810 may make indirect contact with the user's body through the cover glass. In this case, electric charges may be stored between the plurality of electrodes 810 and the user's body (or the cover glass).

According to an embodiment of the present disclosure, the plurality of electrodes 810 may include a first electrode 811, a second electrode 812, a third electrode 813, and a fourth electrode 814. Unless otherwise noted, the descriptions of the first to fourth electrodes 411 to 414 may also be applied to the first to fourth electrodes 811 to 814.

The plurality of sensors 820 may include an optical sensor 821, a GSR sensor 822, an ECG sensor 823, and a BIA sensor 824. The optical sensor 821 may obtain a PPG on the basis of light reflected by the user's body. Electrode sensors, such as the GSR sensor 822, the ECG sensor 823, and the BIA sensor 824, may obtain a GSR, an ECG, and a BIA on the basis of current flowing through the plurality of electrodes 810, or capacitance between the plurality of electrodes 810 and the user's body.

The sensor controller 830 may be electrically connected with the plurality of electrodes 810, the plurality of sensors 820, and the processor 850. The sensor controller 830 may control the optical sensor 821, the GSR sensor 822, and the ECG sensor 823 on the basis of signals received from the processor 850.

The memory 840 may store program modules. The memory 840 may store a wearing detection module 841, a contact determination module 842, an HR measurement module 843, a BIA measurement module 844, an ECG measurement module 845, and a GSR measurement module 846.

The aforementioned program modules may be executed by the processor 850. The wearing detection module 841, when executed, may detect whether the electronic device 800 is worn. The contact determination module 842, when executed, may determine whether the user's body (e.g., a finger) is brought into contact with the electronic device 800. The HR measurement module 843, when executed, may measure the user's HR. The BIA measurement module 844, when executed, may measure the user's BIA. The ECG measurement module 845, when executed, may measure the user's ECG. The GSR measurement module 846, when executed, may measure the user's GSR.

The display 860 may output biometric information measured by the program modules.

The communication module 870 may transmit the biometric information measured by the program modules to another electronic device (e.g., a PC, a smartphone, etc.).

The PMIC 880 may charge a battery in the case where the electronic device 800 is not worn. In contrast, the PMIC 880 may supply power stored in the battery to the modules and the sensors in the case where the electronic device 800 is worn.

According to an embodiment of the present disclosure, an electronic device includes a display including a plurality of electrodes selectively connectable to a touch sensor or one or more biometric sensors, and a processor. The processor may receive an input through the plurality of electrodes in a state in which the touch sensor and the plurality of electrodes are connected, may perform an operation corresponding to the input relating to the touch sensor in a case where the input satisfies a first condition, may connect the plurality of electrodes to the one or more biometric sensors in a case where the input satisfies a second condition, and may obtain a plurality of pieces of biometric information through the plurality of electrodes connected with the one or more biometric sensors.

According to an embodiment of the present disclosure, the electronic device may further include one or more switch circuits that selectively connect the plurality of electrodes and the one or more biometric sensors.

According to an embodiment of the present disclosure, the processor may electrically connect the plurality of electrodes, and the one or more biometric sensors by switching the switching circuits according to the pre-determined sequence and may obtain the plurality of pieces of biometric information according to the pre-determined sequence.

According to an embodiment of the present disclosure, the processor may detect a user's wearing the electronic device or contact of the user's body with the electronic device through the touch sensor.

According to an embodiment of the present disclosure, the processor may obtain the biometric information in a state in which the wearing is detected and the contact is maintained.

According to an embodiment of the present disclosure, the electronic device may further include an optical sensor, and the processor may obtain a SpO2, a PPG, or an HR through the optical sensor in a case where the user input satisfies the first condition.

According to an embodiment of the present disclosure, the processor may connect the plurality of electrodes to the one or more sensors if biometric information measured through the optical sensor is within a pre-determined range.

According to an embodiment of the present disclosure, the processor may obtain a GSR, an ECG, a BIA, an EMG, an EEG, or an EOG in a case where the user input satisfies the second condition.

According to an embodiment of the present disclosure, the plurality of electrodes may include a first electrode and a second electrode, and the processor may change a state of obtaining the biometric information, based on a time difference of contact of a user's body with the first electrode and the second electrode.

According to an embodiment of the present disclosure, the processor may obtain the plurality of pieces of biometric information if a user's body is brought into contact with the electronic device for a pre-determined period of time or longer.

According to an embodiment of the present disclosure, the processor may obtain the plurality of pieces of biometric information if a strength by which a user's body is brought into contact with the electronic device is greater than or equal to a pre-determined value.

According to an embodiment of the present disclosure, the electronic device may further include a motor, and the processor may vibrate the motor if contact of a user's body with the electronic device is detected through the touch sensor.

According to an embodiment of the present disclosure, the electronic device may further include a communication circuit that transmits the obtained biometric information to an external device.

According to an embodiment of the present disclosure, an electronic device includes a housing including a first electrode or a second electrode, a first sensor selectively connectable to the first or second electrode, a second sensor selectively connectable to the first or second electrode, and a processor. The processor may receive an input for measuring biometric information through the first or second electrode, may connect the first or second electrode with the first sensor based at least on the input, may obtain first biometric information relating to the first sensor through at least one electrode connected with the first sensor, may connect the first or second electrode with the second sensor after obtaining the first biometric information, and may obtain second biometric information relating to the second sensor through an electrode connected with the second sensor.

According to an embodiment of the present disclosure, the electronic device may further include one or more switches that selectively connect the first or second electrode with the first or second sensor.

According to an embodiment of the present disclosure, the processor may identify the first or second biometric information satisfying a first condition and may re-obtain the first or second biometric information satisfying the first condition by connecting the first or second electrode to the first or second sensor, based on the identification result.

According to an embodiment of the present disclosure, the processor may provide a display or an external device with the first condition under which the first or second biometric information is not obtained.

According to an embodiment of the present disclosure, the processor may re-obtain the first or second biometric information by connecting the first or second electrode to the first or second sensor for a pre-determined period of time or longer, based at least on the identification result.

According to an embodiment of the present disclosure, the processor may re-obtain the first or second biometric information by amplifying a signal for re-obtaining the first or second biometric information to a pre-determined strength or higher based at least one of the identification result and then transmitting the amplified signal to the first or second sensor.

According to an embodiment of the present disclosure, the housing may accommodate at least a part of a display in which the first or second electrode is disposed, and the display may output the first or second biometric information.

Figure 9:
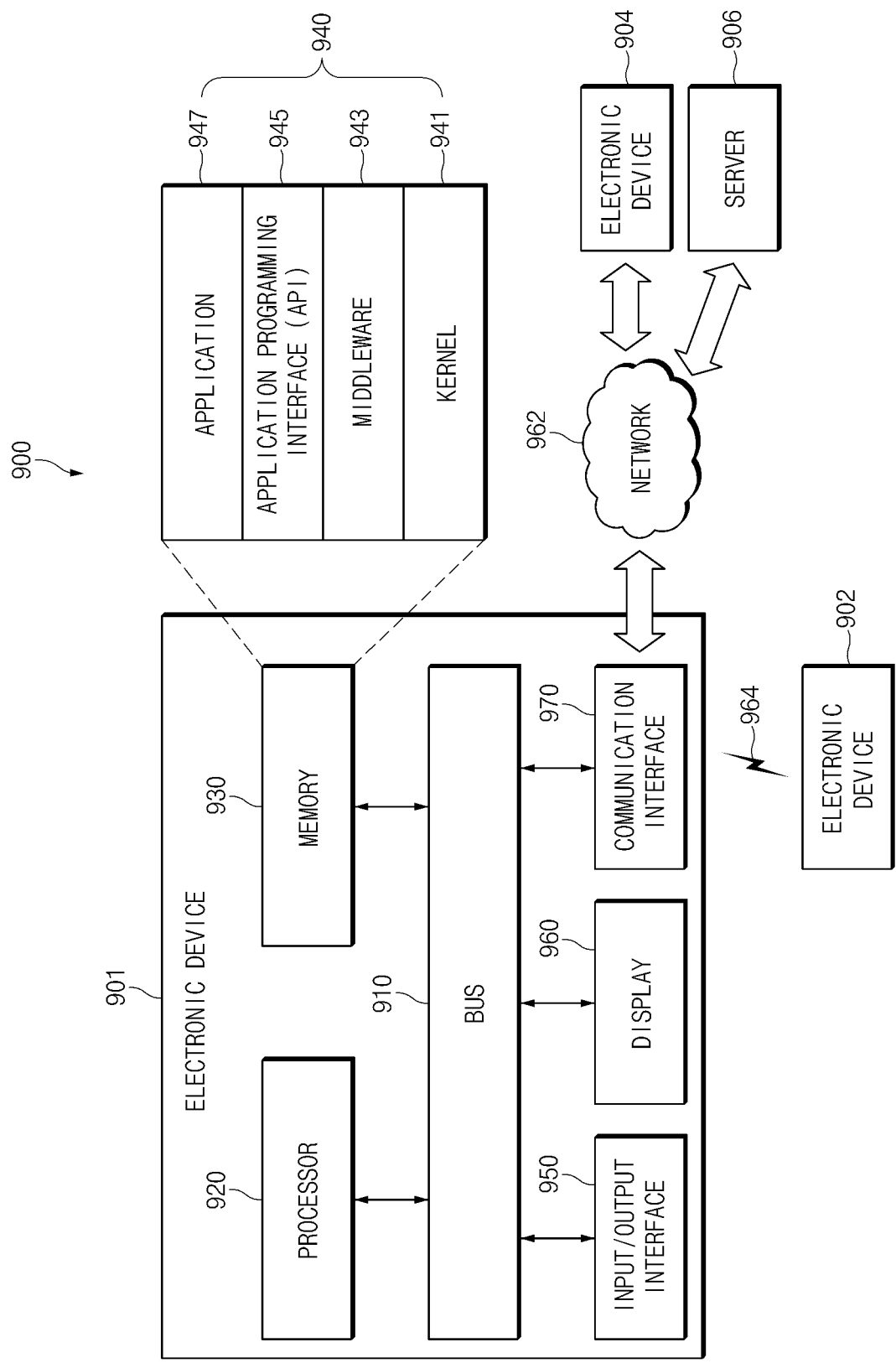
FIG. 9 is a block diagram illustrating an electronic device in a network environment, according to various embodiments of the present disclosure.

FIG. 9 is a block diagram illustrating an electronic device 901 in a network environment 900, according to various embodiments of the present disclosure. Referring to FIG. 9 an electronic device 901 in a network environment 900 may communicate with an electronic device 902 via a first network 964 (e.g., a short-range wireless communication network), or an electronic device 904 or a server 906 via a second network 962 (e.g., a long-range wireless communication network). The electronic device 901 may communicate with the electronic device 904 via the server 906. The electronic device 901 may include a bus 910, a processor 920, a memory 930, an input/output interface 950, a display 960, and a communication interface 970. The electronic device 901 may not include at least one of the above-described elements or may further include other element(s).

The bus 910 may interconnect the above-described elements 920 to 970 and may include a circuit for conveying communications (e.g., a control message and/or data) among the above-described elements.

The processor 920 may execute, for example, software (e.g., a program 940) to control at least one other component (e.g., a hardware or software component) of the electronic device 901 coupled with the processor 920, and may perform various data processing or computation. According to one embodiment of the present disclosure, as at least part of the data processing or computation, the processor 920 may load a command or data received from another component (e.g., the input/output interface 950 or the communication interface 970) in volatile memory, process the command or the data stored in the volatile memory, and store resulting data in non-volatile memory. The processor 920 may include a main processor (e.g., a CPU or an AP), and an auxiliary processor (e.g., a graphics processing unit (GPU), an image signal processor (ISP), a sensor hub processor, or a CP) that is operable independently from, or in conjunction with, the main processor. Additionally or alternatively, the auxiliary processor may be adapted to consume less power than the main processor, or to be specific to a specified function. The auxiliary processor may be implemented as separate from, or as part of the main processor.

The auxiliary processor may control at least some of functions or states related to at least one component (e.g., the display 960, the input/output interface 950, or the communication interface 970) among the components of the electronic device 901, instead of the main processor while the main processor is in an inactive (e.g., sleep) state, or together with the main processor while the main processor is in an active state (e.g., executing an application). According to an embodiment of the present disclosure, the auxiliary processor3 (e.g., an image signal processor or a communication processor) may be implemented as part of another component (e.g., the input/output interface 950 or the communication interface 970)) functionally related to the auxiliary processor #23.

The processor 920 may perform an arithmetic operation or data processing associated with control and/or communication of other elements of the electronic device 901.

The memory 930 may store various data used by at least one component (e.g., the processor 920 or the input/output interface 950) of the electronic device 901. The various data may include, for example, software (e.g., the program 940) and input data or output data for a command related thereto. The memory 930 may include the volatile memory or the non-volatile memory.

The program 940 may be stored in the memory 930 as software, and may include, for example, an operating system (OS), a kernel 941, a middleware 943, application programming interface (API) 945, or an application 947. The kernel 941 may control or manage system resources (e.g., the bus 910, the processor 920, the memory 930, etc.) that are used to execute operations or functions of other programs (e.g., the middleware 943, the API 945, and the application 947). Furthermore, the kernel 941 may provide an interface that allows the middleware 943, the API 945, or the application 947 to access discrete elements of the electronic device 901 so as to control or manage system resources.

The middleware 943 may perform a mediation role such that the API 945 or the application 947 communicates with the kernel 941 to exchange data.

Furthermore, the middleware 943 may process task requests received from the application 947 according to a priority. The middleware 943 may assign the priority, which makes it possible to use a system resource (e.g., the bus 910, the processor 920, the memory 930, etc.) of the electronic device 901, to one of the applications 947. The middleware 943 may process the one or more task requests according to the priority assigned to each task, which makes it possible to perform scheduling or load balancing on the one or more task requests.

The API 945 may be an interface through which the application 947 controls a function provided by the kernel 941 or the middleware 943, and may include at least one interface or function (e.g., an instruction) for a file control, a window control, image processing, a character control, etc.

The input/output interface 950 may receive a command or data to be used by other component (e.g., the processor 920) of the electronic device 901, from the outside (e.g., a user) of the electronic device 901. Furthermore, the input/output interface 950 may output an instruction or data, received from other element(s) of the electronic device 901, to a user or another external device. The input/output interface 950 may include, for example, a microphone, a mouse, or a keyboard.

The display device 960 may visually provide information to the outside (e.g., a user) of the electronic device 901. The display device 960 may include, for example, a display, a hologram device, or a projector and control circuitry to control a corresponding one of the display, hologram device, and projector. According to an embodiment of the present disclosure, the display device #60 may include touch circuitry adapted to detect a touch, or sensor circuitry (e.g., a pressure sensor) adapted to measure the intensity of force incurred by the touch. The display device 960 may include a liquid crystal display (LCD), a light-emitting diode (LED) display, an organic LED (OLED) display, a micro electro mechanical systems (MEMS) display, or an electronic paper display. The display device 960 may display various contents (e.g., a text, an image, a video, an icon, a symbol, etc.) to a user. The display device 960 may include a touch screen and may receive a touch, a gesture, or a proximity or hovering input using an electronic pen or a part of a user's body.

The communication interface 970 may support one or more specified protocols to be used for the electronic device 901 to be coupled with the external electronic device (e.g., the electronic device 902) directly (e.g., wiredly) or wirelessly. According to an embodiment of the present disclosure, the communication interface 970 may include, for example, a high definition multimedia interface (HDMI), a universal serial bus (USB) interface, a secure digital (SD) card interface, or an audio interface.

The wireless communication may use long-term evolution (LTE), LTE advanced (LTE-A), code division multiple access (CDMA), wideband CDMA (WCDMA), universal mobile telecommunications system (UMTS), wireless broadband (WiBro), global system for mobile communications (GSM), etc. According to an embodiment of the present disclosure, the wireless communication may include wireless fidelity (Wi-Fi), light fidelity (Li-Fi), Bluetooth™, Bluetooth low energy (BLE), near field communication (NFC), magnetic stripe transmission (MST), radio frequency (RF), body area network (BAN), GNSS, etc. as the short range communication 964.

The MST may generate a pulse in response to transmission data using an electromagnetic signal, and the pulse may generate a magnetic field signal. The electronic device 901 may transfer the magnetic field signal to a POS device, and the POS device may detect the magnetic field signal using a MST reader. The POS device may recover the data by converting the detected magnetic field signal to an electrical signal.

The GNSS may include a global positioning system (GPS), a global navigation satellite system (Glonass), a Beidou navigation satellite system (Beidou), or an European global satellite-based navigation system (Galileo) based on an available region, a bandwidth, etc. Hereinafter, in the present disclosure, the terms "GPS" and "GNSS" may be interchangeably used. The wired communication may include a USB, a HDMI, a recommended standard-232 (RS-232), a plain old telephone service (POTS), etc. The network 962 may include telecommunications networks, for example, a computer network (e.g., local area network (LAN) or wide area network (WAN)), an Internet, or a telephone network.

Each of the electronic devices 902 and 904 may be a device of which the type is different from or the same as that of the electronic device 901. According to an embodiment short range communication, the server 906 may include a group of one or more servers. All or a portion of operations that the electronic device 901 will perform may be executed by another or a plurality of electronic devices (e.g., the electronic device 902, the second electronic device 904, or the server 906). In the case where the electronic device 901 executes any function or service automatically or in response to a request, the electronic device 901 may not perform the function or the service internally, but, alternatively or additionally, may request a portion of a function associated with the electronic device 901 from another device. The other electronic device may execute the requested function or additional function, and may transmit the execution result to the electronic device 901. The electronic device 901 may provide the requested function or service using the received result or may additionally process the received result to provide the requested function or service. For this purpose cloud computing, distributed computing, or client-server computing may be used.

Figure 10:
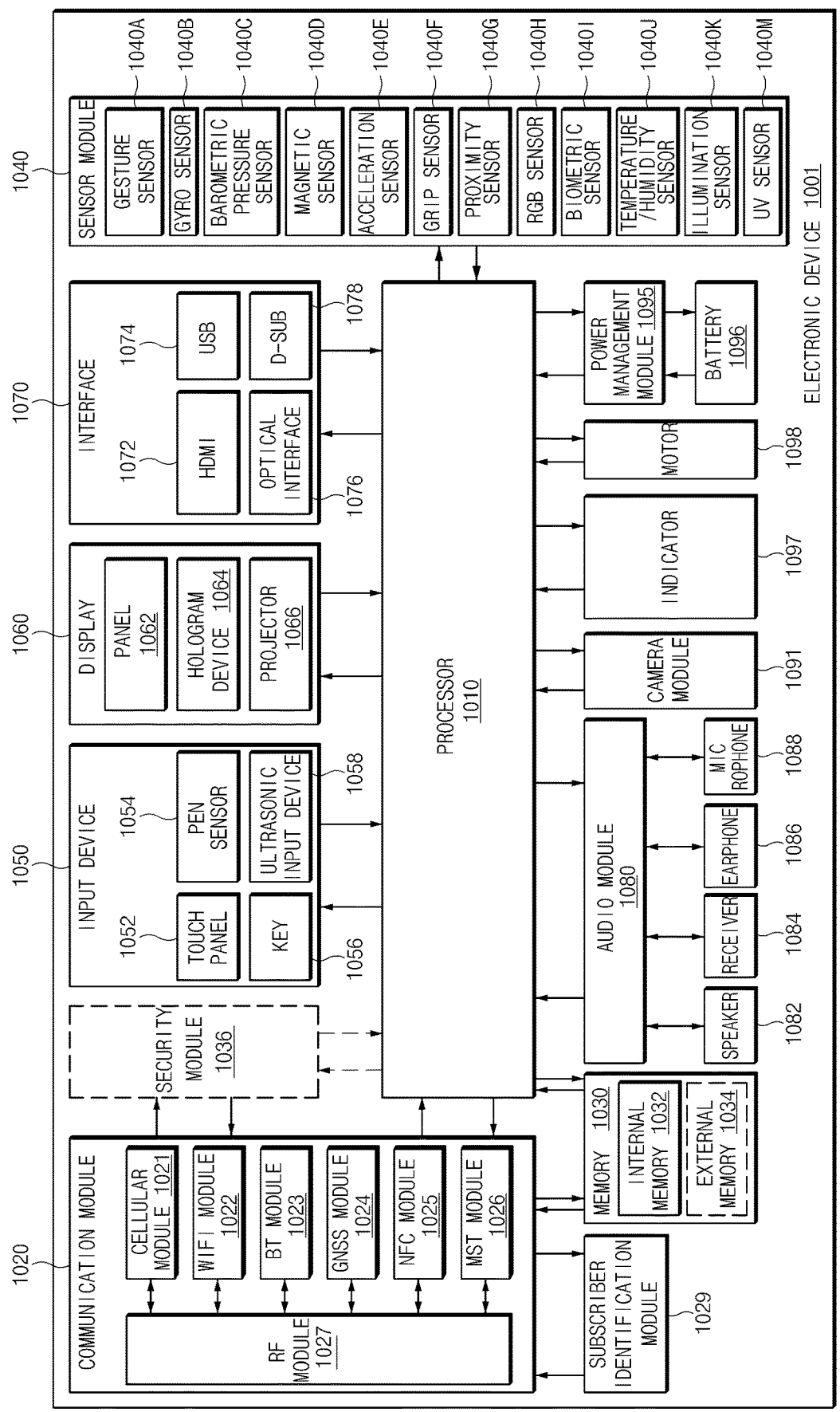
FIG. 10 is a block diagram of an electronic device, according to various embodiments of the present disclosure.

FIG. 10 illustrates a block diagram of an electronic device, according to various embodiments short range communication.

Referring to FIG. 10, an electronic device 1001 may include all or a part of the electronic device 901. The electronic device 1001 may include one or more processors 1010 (e.g., an AP), a communication module 1020, a subscriber identification module (SIM) 1029, a memory 1030, a sensor module 1040, an input device 1050, a display 1060, an interface 1070, an audio module 1080, a camera module 1091, a power management module 1095, a battery 1096, an indicator 1097, and a motor 1098.

The processor 1010 may drive an OS or an application to control a plurality of hardware or software elements connected to the processor 1010 and may process and compute a variety of data. The processor 1010 may be implemented with a system on chip (SoC). According to an embodiment short range communication, the processor 1010 may further include a GPU and/or an ISP. The processor 1010 may include at least a part (e.g., a cellular module 1021) of electronic device 1001. The processor 1010 may load an instruction or data, which is received from other elements (e.g., a nonvolatile memory), into a volatile memory and process the loaded instruction or data. The processor 1010 may store a variety of data in the nonvolatile memory.

The communication module 1020 may be configured the same as or similar to the communication interface 970. The communication module 1020 may include the cellular module 1021, a Wi-Fi module 1022, a Bluetooth (BT) module 1023, a GNSS module 1024 (e.g., a GPS module, a Glonass module, a Beidou module, or a Galileo module), a NFC module 1025, a MST module 1026, and an RF module 1027.

The cellular module 1021 may provide voice communication, video communication, a character service, an Internet service, etc. over a communication network. According to an embodiment of the present disclosure, the cellular module 1021 may perform discrimination and authentication of the electronic device 1001 within a communication network by using the SIM 1029 (e.g., a SIM card). The cellular module 1021 may perform a portion of functions that the processor 1010 provides. The cellular module 1021 may include a CP.

Each of the Wi-Fi module 1022, the BT module 1023, the GNSS module 1024, the NFC module 1025, or the MST module 1026 may include a processor for processing data exchanged through a corresponding module. According to an embodiment of the present disclosure, a part (e.g., two or more) of the cellular module 1021, the Wi-Fi module 1022, the BT module 1023, the GNSS module 1024, the NFC module 1025, or the MST module 1026 may be included within one integrated circuit (IC) or an IC package.

The RF module 1027 may transmit and receive a communication signal (e.g., an RF signal). The RF module 1027 may include a transceiver, a power amplifier module (PAM), a frequency filter, a low noise amplifier (LNA), an antenna, etc. According to an embodiment of the present disclosure, at least one of the cellular module 1021, the Wi-Fi module 1022, the BT module 1023, the GNSS module 1024, the NFC module 1025, or the MST module 1026 may transmit and receive an RF signal through a separate RF module.

The SIM 1029 may include a card and/or embedded SIM that includes a SIM and may include unique identify information (e.g., integrated circuit card identifier (ICCID)) or subscriber information (e.g., integrated mobile subscriber identity (IMSI)).

The memory 1030 may include an internal memory 1032 or an external memory 1034. The internal memory 1032 may include a volatile memory (e.g., a dynamic random access memory (DRAM), a static RAM (SRAM), a synchronous DRAM (SDRAM), etc.), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory), etc.), a hard drive, or a solid state drive (SSD).

The external memory 1034 may further include a flash drive such as compact flash (CF), SD, micro secure digital (Micro-SD), mini secure digital (Mini-SD), extreme digital (xD), a multimedia card (MMC), a memory stick, etc. The external memory 1034 may be operatively and/or physically connected to the electronic device 1001 through various interfaces.

A security module 1036 may be a module that includes a storage space of which a security level is higher than that of the memory 1030 and may be a circuit that guarantees safe data storage and a protected execution environment. The security module 1036 may be implemented with a separate circuit and may include a separate processor. The security module 1036 may be in a smart card or a SD card, which is removable, or may include an embedded secure element (eSE) embedded in an IC chip of the electronic device 1001. Furthermore, the security module 1036 may operate based on an OS that is different from the OS of the electronic device 1001. For example, the security module 1036 may operate based on java card open platform (JCOP) OS.

The sensor module 1040 may measure a physical quantity or may detect an operation state of the electronic device 1001. The sensor module 1040 may convert the measured or detected information to an electric signal. The sensor module 1040 may include a gesture sensor 1040A, a gyro sensor 1040B, a barometric pressure sensor 1040C, a magnetic sensor 1040D, an acceleration sensor 1040E, a grip sensor 1040F, the proximity sensor 1040G, a color sensor 1040H (e.g., red, green, blue (RGB) sensor), a biometric sensor 1040I, a temperature/humidity sensor 1040J, an illuminance sensor 1040K, or an UV sensor 1040M. Additionally or generally, the sensor module 1040 may further include an E-nose sensor, an EMG sensor, an EEG sensor, an ECG sensor, an infrared (IR) sensor, an iris sensor, and/or a fingerprint sensor. The sensor module 1040 may further include a control circuit for controlling one or more sensors included therein. According to an embodiment of the present disclosure, the electronic device 1001 may further include a processor that is a part of the processor 1010 or independent of the processor 1010, and is configured to control the sensor module 1040. The processor may control the sensor module 1040 while the processor 1010 remains at a sleep state.

The input device 1050 may include a touch panel 1052, a (digital) pen sensor 1054, a key 1056, or an ultrasonic input unit 1058. The touch panel 1052 may use a capacitive type, a resistive type, an infrared type, and an ultrasonic type. Also, the touch panel 1052 may further include a control circuit. The touch panel 1052 may further include a tactile layer to provide a tactile reaction to a user.

The (digital) pen sensor 1054 may be a part of a touch panel or may include an additional sheet for recognition. The key 1056 may include a physical button, an optical key, a keypad, etc. The ultrasonic input device 1058 may detect (or sense) an ultrasonic signal, which is generated from an input device, through a microphone 1088 and may check data corresponding to the detected ultrasonic signal.

The display 1060 may include a panel 1062, a hologram device 1064, or a projector 1066. The panel 1062 may be the same as or similar to the display 960. The panel 1062 may be implemented to be flexible, transparent, or wearable. The panel 1062 and the touch panel 1052 may be integrated into a single module. The hologram device 1064 may display a stereoscopic image in a space using a light interference phenomenon. The projector 1066 may project light onto a screen so as to display an image. The screen may be arranged in the inside or the outside of the electronic device 1001. According to an embodiment of the present disclosure, the display 1060 may further include a control circuit for controlling the panel 1062, the hologram device 1064, or the projector 1066.

The interface 1070 may include an HDMI 1072, a USB 1074, an optical interface 1076, or a D-subminiature (D-sub) 1078. The interface 1070 may be included in the communication interface 970. Additionally or generally, the interface 1070 may include a mobile high definition link (MHL) interface, a SD card/MMC interface, or an Infrared Data Association (IrDA) standard interface.

The audio module 1080 may convert a sound and an electric signal in dual directions. Part of the audio module 1080 may be included in the input/output interface 950. The audio module 1080 may process sound information that is input or output through a speaker 1082, a receiver 1084, an earphone 1086, or the microphone 1088.

The camera module 1091 may shoot a still image or a video. According to an embodiment of the present disclosure, the camera module 1091 may include one or more image sensors (e.g., a front sensor or a rear sensor), a lens, an ISP, or a flash (e.g., an LED or a xenon lamp).

The power management module 1095 may manage power of the electronic device 1001. According to an embodiment of the present disclosure, a PMIC, a charger IC, or a battery gauge may be included in the power management module 1095. The PMIC may have a wired charging method and/or a wireless charging method. The wireless charging method may include a magnetic resonance method, a magnetic induction method, or an electromagnetic method, and may further include an additional circuit, for example, a coil loop, a resonant circuit, or a rectifier, etc. The battery gauge may measure a remaining capacity of the battery 1096 and a voltage, current, or temperature thereof while the battery is charged. The battery 1096 may include a rechargeable battery and/or a solar battery.

The indicator 1097 may display a specific state of the electronic device 1001 or a part thereof (e.g., the processor 1010), such as a booting state, a message state, a charging state, etc. The motor 1098 may convert an electrical signal into a mechanical vibration and may generate vibration, haptic effects, etc. A processing device (e.g., a GPU) for supporting a mobile TV may be included in the electronic device 1001. The processing device for supporting the mobile TV may process media data according to the standards of digital multimedia broadcasting (DMB), digital video broadcasting (DVB), MediaFlo™, etc.

Each of the above-mentioned elements of the electronic device according to various embodiments of the present disclosure may be configured with one or more components, and the names of the elements may be changed according to the type of the electronic device. The electronic device may include at least one of the above-mentioned elements, and some elements may be omitted or other additional elements may be added. Furthermore, some of the elements of the electronic device may be combined with each other so as to form one component, so that the functions of the elements may be performed in the same manner as before the combination.

Figure 11:
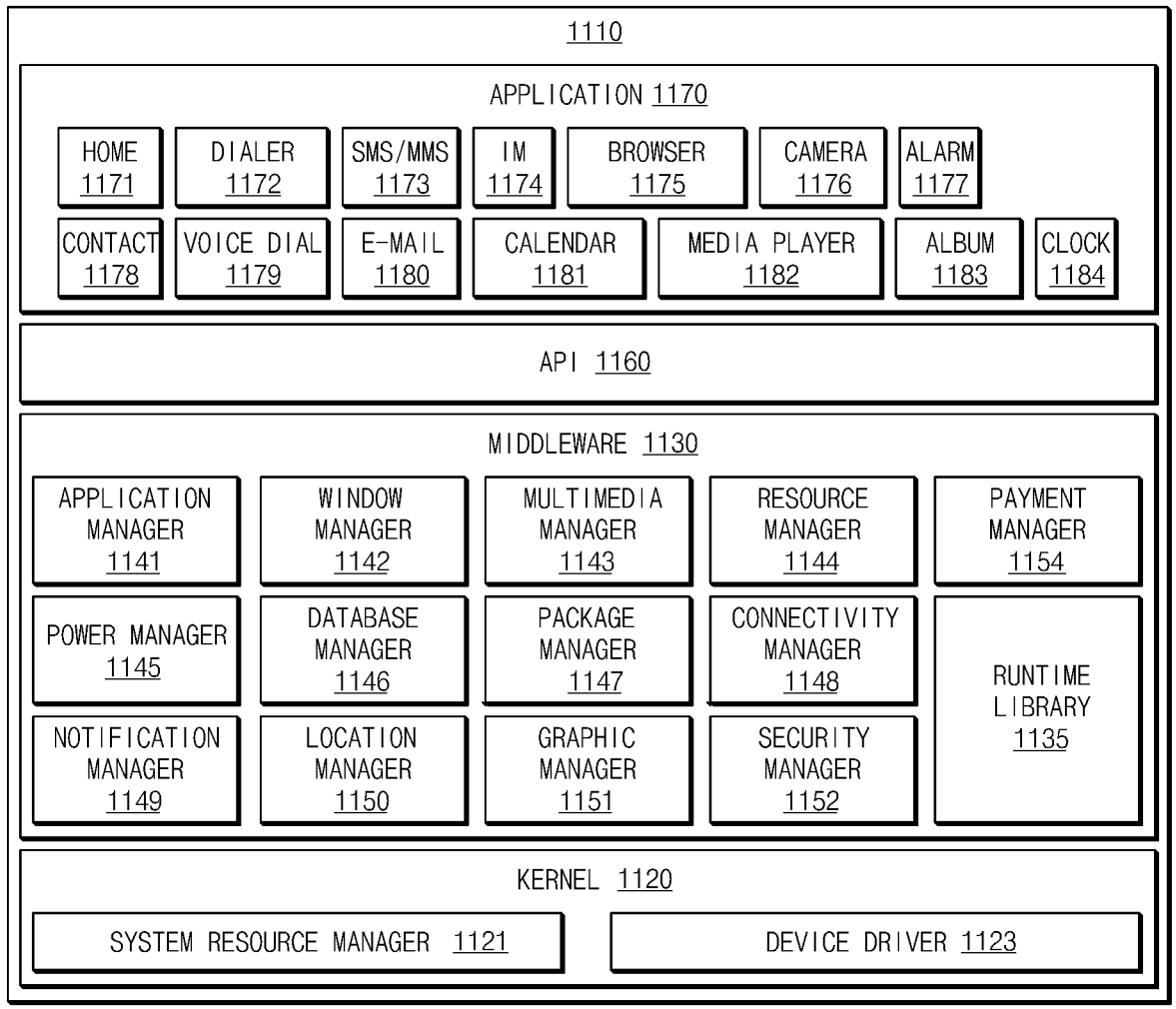
FIG. 11 is a block diagram of a program module, according to various embodiments of the present disclosure.

FIG. 11 is a block diagram of a program module 1110, according to various embodiments. According to an embodiment of the present disclosure, the program module 1110 may include an OS to control on or more resources associated of the electronic device 901, middleware 1130, an API 1160, application 170, or kernel 1120 executable in the OS. The OS may include, for example, Android™, iOS™, Windows™, Symbian™, Tizen™, or Bada™. At least part of the program module 1110, for example, may be preloaded on the electronic device 901 during manufacture, or may be downloaded from or updated by an external electronic device (e.g., the electronic device 902 or 904, or the server 906) during use by a user.

The OS may control management (e.g., allocating or deallocation) of one or more system resources (e.g., process, memory, or power source) of the electronic device 901. The OS, additionally or alternatively, may include one or more driver programs to drive other hardware devices of the electronic device 901.

The program module 1110 may include a kernel 1120, a middleware 1130, an API 1160, and/or an application 1170. A portion of the program module 1110 may be preloaded on an electronic device or may be downloadable from an external electronic device (e.g., the electronic device 902, the second electronic device 904, the server 906, etc.).

The kernel 1120 may include a system resource manager 1121 or a device driver 1123. The system resource manager 1121 may perform control, allocation, or retrieval of system resources. According to an embodiment of the present disclosure, the system resource manager 1121 may include a process managing unit, a memory managing unit, or a file system managing unit. The device driver 1123 may include a display driver, a camera driver, a BT driver, a shared memory driver, a USB driver, a keypad driver, a Wi-Fi driver, an audio driver, or an inter-process communication (IPC) driver.

The middleware 1130 may provide a function that the application 1170 needs in common, or may provide various functions to the application 1170 through the API 1160 to allow the application 1170 to efficiently use limited system resources of the electronic device. According to an embodiment of the present disclosure, the middleware 1130 may include a runtime library 1135, an application manager 1141, a window manager 1142, a multimedia manager 1143, a resource manager 1144, a power manager 1145, a database manager 1146, a package manager 1147, a connectivity manager 1148, a notification manager 1149, a location manager 1150, a graphic manager 1151, a security manager 1152, or a payment manager 1154.

The runtime library 1135 may include a library module that is used by a compiler to add a new function through a programming language while the application 1170 is being executed. The runtime library 1135 may perform input/output management, memory management, or capacities about arithmetic functions.

The application manager 1141 may manage a life cycle of at least one application of the application 1170. The window manager 1142 may manage a graphic user interface (GUI) resource that is used in a screen. The multimedia manager 1143 may identify a format necessary for playing various media files, and may perform encoding or decoding of media files by using a codec suitable for the format. The resource manager 1144 may manage resources such as a storage space, memory, or source code of at least one application of the application 1170.

The power manager 1145 may operate with a basic input/output system (BIOS) to manage a battery or power, and may provide power information for an operation of an electronic device. The database manager 1146 may generate, search for, or modify a database that is to be used in at least one application of the application 1170. The package manager 1147 may install or update an application that is distributed in the form of a package file.

The connectivity manager 1148 may manage a wireless connection such as Wi-Fi or Bluetooth. The notification manager 1149 may display or notify an event such as arrival message, appointment, or proximity notification in a mode that does not disturb a user. The location manager 1150 may manage location information about an electronic device. The graphic manager 1151 may manage a graphic effect that is provided to a user, or manage a user interface relevant thereto. The security manager 1152 may provide a general security function necessary for system security, user authentication, etc. According to an embodiment of the present disclosure, in the case where an electronic device 901 includes a telephony function, the middleware 1130 may further include a telephony manager for managing a voice or video call function of the electronic device.

The middleware 1130 may include a middleware module that combines various functions of the above-described elements. The middleware 1130 may provide a module specialized to each OS type to provide differentiated functions. Additionally, the middleware 1130 may dynamically remove a part of the preexisting elements or may add new elements thereto.

The API 1160 may be a set of programming functions and may be provided with a configuration that is variable depending on the type of the OS. In the case where an OS is Android or iOS, one API set per platform may be provided. In the case where an OS is Tizen, two or more API sets per platform may be provided.

The application 1170 may include one or more applications capable of providing functions for a home 1171 application, a dialer 1172 application, an SMS/MMS 1173 application, an instant message (IM) 1174 application, a browser 1175 application, a camera 1176 application, an alarm 1177 application, a contact 1178 application, a voice dial 1179 application, an e-mail 1180 application, a calendar 1181 application, a media player 1182 application, an album 1183 application, a clock 1184 application, a healthcare application (e.g., measuring an exercise quantity, blood sugar level, etc.) or an application offering environment information (e.g., information of barometric pressure, humidity, temperature, etc.).

The device management application may control the power (e.g., turn-on or turn-off) or the function (e.g., adjustment of brightness, resolution, or focus) of the external electronic device or some component thereof (e.g., a display device or a camera module of the external electronic device). The device management application, additionally or alternatively, may support installation, delete, or update of an application running on the external electronic device.

According to an embodiment of the present disclosure, the application 1170 may include an information exchanging application to support information exchange between an electronic device and an external electronic device. The information exchanging application may include a notification relay application for transmitting specific information to an external electronic device, or a device management application for managing the external electronic device.

The notification relay application may include a function of transmitting notification information, which arise from other applications (e.g., applications for SMS/MMS, e-mail, healthcare, or environmental information), to an external electronic device. Additionally, the information exchanging application may receive notification information from an external electronic device and provide the notification information to a user.

The device management application may manage (e.g., install, delete, or update) at least one function (e.g., turn-on/turn-off of an external electronic device itself (or a part of elements) or adjustment of brightness (or resolution) of a display) of the external electronic device which communicates with the electronic device, an application running in the external electronic device, or a service (e.g., a call service, a message service, etc.) provided from the external electronic device.

According to an embodiment of the present disclosure, the application 1170 may include an application (e.g., a healthcare application of a mobile medical device) that is assigned in accordance with an attribute of an external electronic device. The application 1170 may include an application that is received from an external electronic device (e.g., the electronic device 902, the second electronic device 904, or the server 906). The application 1170 may include a preloaded application or a third party application that is downloadable from a server. The names of elements of the program module 1110 may be modifiable depending on the type of the OS.

According to various embodiments of the present disclosure, the program module 1110 may be implemented by software, firmware, hardware, or a combination of two or more thereof. At least a portion of the program module 1110 may be implemented (e.g., executed) by the processor 1010. At least a portion of the program module 1110 may include modules, programs, routines, sets of instructions, processes, etc. for performing one or more functions.

A computer-readable recording medium may include a hard disk, a floppy disk, a magnetic media (e.g., a magnetic tape), an optical media (e.g., a compact disc read only memory (CD-ROM) and a DVD, a magneto-optical media (e.g., a floptical disk)), and hardware devices (e.g., a read only memory (ROM), a random access memory (RAM), or a flash memory). Also, a program instruction may include not only assembly code such as things generated by a compiler but also a high-level language code executable on a computer using an interpreter. The above hardware unit may be configured to operate via one or more software modules for performing an operation according to various embodiments, and vice versa.

According to various embodiments of the present disclosure, a module or a program module may include at least one of the above elements, or a part of the above elements may be omitted, or additional other elements may be further included. Operations performed by a module, a program module, or other elements according to various embodiments may be executed sequentially, in parallel, repeatedly, or in a heuristic method. In addition, some operations may be executed in different sequences or may be omitted. Alternatively, other operations may be added.

Various embodiments disclosed herein are provided merely to easily describe technical details of the present disclosure and to help the understanding of the present disclosure, and are not intended to limit the scope of the present disclosure. Accordingly, the scope of the present disclosure should be construed as including all modifications or various other embodiments based on the technical idea of the present disclosure as defined in the appended claims and their equivalents.

What is claimed is:

1. An electronic device comprising:
a plurality of electrodes;
a front surface including a first electrode of the plurality of electrodes and a second electrode of the plurality of electrodes;
a rear surface including a third electrode of the plurality of electrodes and a fourth electrode of the plurality of electrodes;
a touch sensor provided on the rear surface, the touch sensor operatively connected with the third electrode and the fourth electrode;
one or more biometric sensors including a first biometric sensor and a second biometric sensor;
a display provided on the front surface;
switching circuitry configured to change a connection between at least a part of the plurality of electrodes and the one or more biometric sensors; and
a processor configured to:
detect, using the touch sensor, wearing of the electronic device by sensing contact with a part of a body of a user through the third electrode and the fourth electrode;
receive a user input through one of the first electrode and the second electrode during the detected contact;
obtain first biometric information through a first connection included in the connection between at least one of the first electrode and the second electrode and the first biometric sensor during a first time period in which the user input is received;
change the first connection to a second connection included in the connection using the switching circuitry based on a pre-determined sequence for obtaining a plurality of biometric information including the first biometric information; and
obtain second biometric information through the second connection between at least one of the third electrode and the fourth electrode and the second biometric sensor during a second time period after the first time period,
wherein the processor is further configured to:
detect sequential touching of the first electrode and the second electrode, while obtaining galvanic skin response (GSR),
change to a state of obtaining an electrocardiography (ECG), based on detecting sequential touching in a first direction from the first electrode to the second electrode while obtaining the GSR, and
return to obtaining GSR from obtaining the ECG, based on detecting sequential touching in a second direction from the second electrode to the first electrode, and
wherein the display is configured to output biometric information obtained via the one or more biometric sensors.

2. The electronic device of claim 1, wherein the processor is further configured to:
   electrically connect the plurality of electrodes and the one or more biometric sensors by connecting at least one switching circuit of the switching circuitry according to the pre-determined sequence, and
   obtain the plurality of biometric information sequentially according to the pre-determined sequence.

3. The electronic device of claim 1, further comprising:
   a motion sensor,
   wherein the processor is further configured to:
      sense a degree of motion of the user using the motion sensor, and
      amplify a strength of one or more signals transmitted through the one or more biometric sensors.

4. The electronic device of claim 1, further comprising:
   a first optical sensor provided through the front surface; and
   a second optical sensor provided through the rear surface.

5. The electronic device of claim 4, wherein the first optical sensor is provided between the first electrode and the second electrode, and
   wherein the second optical sensor is provided between the third electrode and the fourth electrode, with the second optical sensor configured to detect contact of a wrist of the user being in contact with the electronic device based on light reflected by the wrist.

6. The electronic device of claim 1, wherein the processor is further configured to obtain, using the second optical sensor, at least one of blood oxygen saturation, photoplethysmograph (PPG), or a heart rate.

7. The electronic device of claim 1, further comprising:
   a battery; and
   a charging circuit,
   wherein, based on identifying that the body of the user does not contact the first electrode, the processor is further configured to:
      electrically connect a part of plurality of electrodes and the charging circuit using the switching circuitry, and
      charge the battery using the electrically connected charging circuit.

8. The electronic device of claim 1, wherein the processor is further configured to:
   obtain the plurality of biometric information if a strength by which the user input is received into the second electrode is greater than or equal to a pre-determined value.

9. The electronic device of claim 1, further comprising:
   a motor,
   wherein the processor is further configured to:
   vibrate the motor during the detected contact.

10. The electronic device of claim 1, further comprising:
    a communication circuit configured to transmit the obtained biometric information to an external device.

* * * * *